United States Patent
Morikawa et al.

(10) Patent No.: US 9,696,262 B2
(45) Date of Patent: Jul. 4, 2017

(54) SUBSTRATE PROCESSING APPARATUS, METHOD OF OPERATING SUBSTRATE PROCESSING APPARATUS, AND STORAGE MEDIUM

(71) Applicant: TOKYO ELECTRON LIMITED, Tokyo (JP)

(72) Inventors: Katsuhiro Morikawa, Koshi (JP); Ikuo Sunaka, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 53 days.

(21) Appl. No.: 14/649,615

(22) PCT Filed: Dec. 5, 2013

(86) PCT No.: PCT/JP2013/082744
§ 371 (c)(1),
(2) Date: Jun. 4, 2015

(87) PCT Pub. No.: WO2014/088078
PCT Pub. Date: Jun. 12, 2014

(65) Prior Publication Data
US 2015/0300960 A1   Oct. 22, 2015

(30) Foreign Application Priority Data
Dec. 7, 2012   (JP) .................................. 2012-268687

(51) Int. Cl.
*G01N 21/88* (2006.01)
*H01L 21/673* (2006.01)
(Continued)

(52) U.S. Cl.
CPC ....... *G01N 21/88* (2013.01); *H01L 21/67265* (2013.01); *H01L 21/67326* (2013.01);
(Continued)

(58) Field of Classification Search
CPC .............. G01N 21/88; H01L 21/67326; H01L 21/67346; H01L 21/67772; H01L 21/67733; H01L 21/67775
(Continued)

(56) References Cited

U.S. PATENT DOCUMENTS 5,239,182 A    8/1993  Tateyama et al.
5,740,059 A *  4/1998  Hirata ............... H01L 21/67259
                                                      414/217
(Continued)

FOREIGN PATENT DOCUMENTS

JP    04-321253 A1    11/1992
JP    11-233461 A1     8/1999
(Continued)

OTHER PUBLICATIONS

Japanese Office Action (Application No. 2012-268687) dated Feb. 2, 2016 (with machine translation).

(Continued)

*Primary Examiner* — Sang Nguyen
(74) *Attorney, Agent, or Firm* — Burr & Brown, PLLC

(57) ABSTRACT

A substrate processing apparatus includes: a load port into which the transport container is carried; a detecting unit that detects storage condition of the substrates which are contained in the transport container, which has been carried into the load port and the lid of which has been removed; a processing unit that processes the substrates removed from the transport container having been carried into the load port; and a control unit. The control unit performs a first step that detects storage condition of the substrates, which are contained in the transport container having been carried into the load port, before the substrates are removed from the transport container to be delivered to the processing unit; a second step that detects storage condition of the substrates, (Continued)

which have been processed in the processing unit and returned to the original transport container, before closing the lid; and a third step that judges whether or not the transport container has an abnormality based on results of the first and second steps.

16 Claims, 21 Drawing Sheets

(51) Int. Cl.
*H01L 21/67* (2006.01)
*H01L 21/677* (2006.01)
(52) U.S. Cl.
CPC .. *H01L 21/67346* (2013.01); *H01L 21/67772* (2013.01); *H01L 21/67733* (2013.01); *H01L 21/67775* (2013.01)
(58) Field of Classification Search
USPC ........... 356/237.1–237.5; 414/331, 225, 783, 414/331.14, 331.18
See application file for complete search history.

(56) References Cited

U.S. PATENT DOCUMENTS

| | | | | |
|---|---|---|---|---|
| 5,768,125 A | * | 6/1998 | Zinger | H01L 21/67796 414/275 |
| 6,043,502 A | * | 3/2000 | Ahn | H01L 21/67265 250/559.37 |
| 6,203,617 B1 | * | 3/2001 | Tanoue | H01L 21/67271 118/320 |
| 6,208,909 B1 | * | 3/2001 | Kato | H01L 21/67265 414/331.14 |
| 6,650,409 B1 | * | 11/2003 | Noguchi | G01N 21/9501 356/237.3 |
| 7,206,663 B2 | * | 4/2007 | Teng | H01L 21/681 700/218 |
| 8,041,450 B2 | * | 10/2011 | Takizawa | H01L 21/68707 700/214 |
| 2003/0201256 A1 | * | 10/2003 | Tauchi | H01J 37/32082 219/121.42 |
| 2006/0181699 A1 | * | 8/2006 | Numakura | H01L 21/67167 356/237.2 |
| 2006/0222478 A1 | * | 10/2006 | Wakabayashi | B65G 47/90 414/225.01 |
| 2009/0323037 A1 | | 12/2009 | Aarts et al. | |
| 2012/0230805 A1 | * | 9/2012 | Yamagishi | H01L 21/67109 414/785 |
| 2014/0064885 A1 | * | 3/2014 | Oyama | H01L 21/67373 414/160 |

FOREIGN PATENT DOCUMENTS

| | | |
|---|---|---|
| JP | 2003-168715 A1 | 6/2003 |
| JP | 2009-302531 A1 | 12/2009 |

OTHER PUBLICATIONS

International Search Report (Application No. PCT/JP2013/082744) dated Mar. 4, 2014.

English Translation of International Preliminary Report on Patentability (Chapter I) (Application No. PCT/JP2013/082744) dated Jun. 18, 2015.

* cited by examiner

SUBSTRATE PROCESSING APPARATUS, METHOD OF OPERATING SUBSTRATE PROCESSING APPARATUS, AND STORAGE MEDIUM

BACKGROUND OF THE INVENTION

Field of the Invention

The present invention relates to a technical field for detecting an abnormality of a transport container, in an apparatus that processes substrates having been carried into the apparatus with the use of the transport container, or in a case where a plural numbers of such apparatuses are used.

Description of Related Art

In a semiconductor manufacturing factory, semiconductor substrates are contained in a transport container, and the transport container is transported to a semiconductor manufacturing apparatus by an automatic guided vehicle (AGV) or an overhead hoist transporter (OHT). The semiconductor manufacturing apparatus includes a carry-in and carry-out port through which semiconductor substrates are carried into and carried out from the transport container, and a processing block that processes the semiconductor substrates. A sealed-type transport container provided on its front face with a lid is most widely used. For 12-inch semiconductor wafers, a transport container abbreviated as FOUP is used. The FOUP includes a resin transport container (container main body), which is provided on its front face with a lid. Two key holes are formed in an outer face of the lid.

The carry-in and carry-out port is usually referred to as load port, which includes a stage onto which the FOUP is placed from outside and a mechanism for removing the lid. There are various semiconductor manufacturing apparatus adapted for respective processes for semiconductor manufacturing, such as a film forming apparatus, an apparatus for forming a mask pattern, an etching apparatus, a cleaning apparatus and so on. Semiconductor substrates are sequentially transported among these apparatuses with the use of the transport container.

Transport containers such as FOUPs are provided by plural manufacturer based on the SEMI standard. However, there may be a transport container out of the SEMI standard. When such an abnormal FOUP is used in a semiconductor manufacturing factory, a scratch damage of a wafer during removal of the wafer from the FOUP or another failure may occur. Although Patent Document 1 discloses a structure for checking storage condition of wafers which is semiconductor substrates contained in a FOUP, the structure cannot solve the above problem.

Patent Document 1: JPH4-321253A

SUMMARY OF THE INVENTION

The present invention has been made under the aforementioned circumstances. The object of the present invention is to provide a technique capable of detecting an abnormality of a transport container for containing substrates and carrying them into a substrate processing apparatus, thereby to avoid any trouble caused by the abnormality.

The present invention is a substrate processing apparatus that removes substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, the substrate processing apparatus including: a load port into which the transport container is carried; a detecting unit that detects storage condition of the substrates which are contained in the transport container, which has been carried into the load port and the lid of which has been removed; a processing unit that processes the substrates removed from the transport container having been carried into the load port; and a control unit that performs a first step that detects storage condition of the substrates, which are contained in the transport container having been carried into the load port, before the substrates are removed from the transport container to be delivered to the processing unit; a second step that detects storage condition of the substrates, which have been processed in the processing unit and returned to the original transport container, before closing the lid; and a third step that judges whether or not the transport container has an abnormality based on results of the first and second steps.

Another invention is a method of operating a substrate processing apparatus that removes substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, the method including: a step that carries the transporting container into the load port and removes the lid; a first detecting step that thereafter detects storage condition of the substrates contained in the transport container, before the substrates are delivered to a processing unit; a step that thereafter removes the substrates from the transport container, processes the substrates in the processing unit, and contains the substrate into the transport container; a second detecting step that thereafter detects storage condition of the substrates contained in the transport container, before the lid is closed; and a judging step that judges whether or not the transporting container has an abnormality based on results of the first and second detecting steps.

A yet another invention is a method of operating a plurality of substrate processing apparatuses that each remove substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, the method including: a step that returns substrates having been processed in one of the substrate processing apparatuses to the transport container placed on a load port; a carry-out inspecting step that thereafter detects storage condition of the substrates contained in the transport container, before the lid is closed; a step that thereafter closes the transport container, and carries the transport container into a load port of another one the substrate processing apparatuses; a step that thereafter removes the lid from the transport container; a carry-in inspecting step that thereafter detects storage condition of the substrates contained in the transport container, before the substrates are delivered to a processing unit; and a judging step that judges whether or not the transporting container has an abnormality based on results of the carry-out inspecting step and the carry-in inspecting step.

In the present invention, the storage condition of the substrates in the transport container is detected at both timings when the transport container is carried into the load port of the substrate processing apparatus and when the substrates having been processed in the substrate processing apparatus are returned to the transport container. Whether or not the transport container has an abnormality is judged based on the both detection results. Thus, an abnormal transport container can be detected, whereby a trouble caused by the abnormality of transport container, such as a scratch damage of a substrate can be prevented.

DETAILED DESCRIPTION OF THE INVENTION

<First Embodiment>

Figure 1:
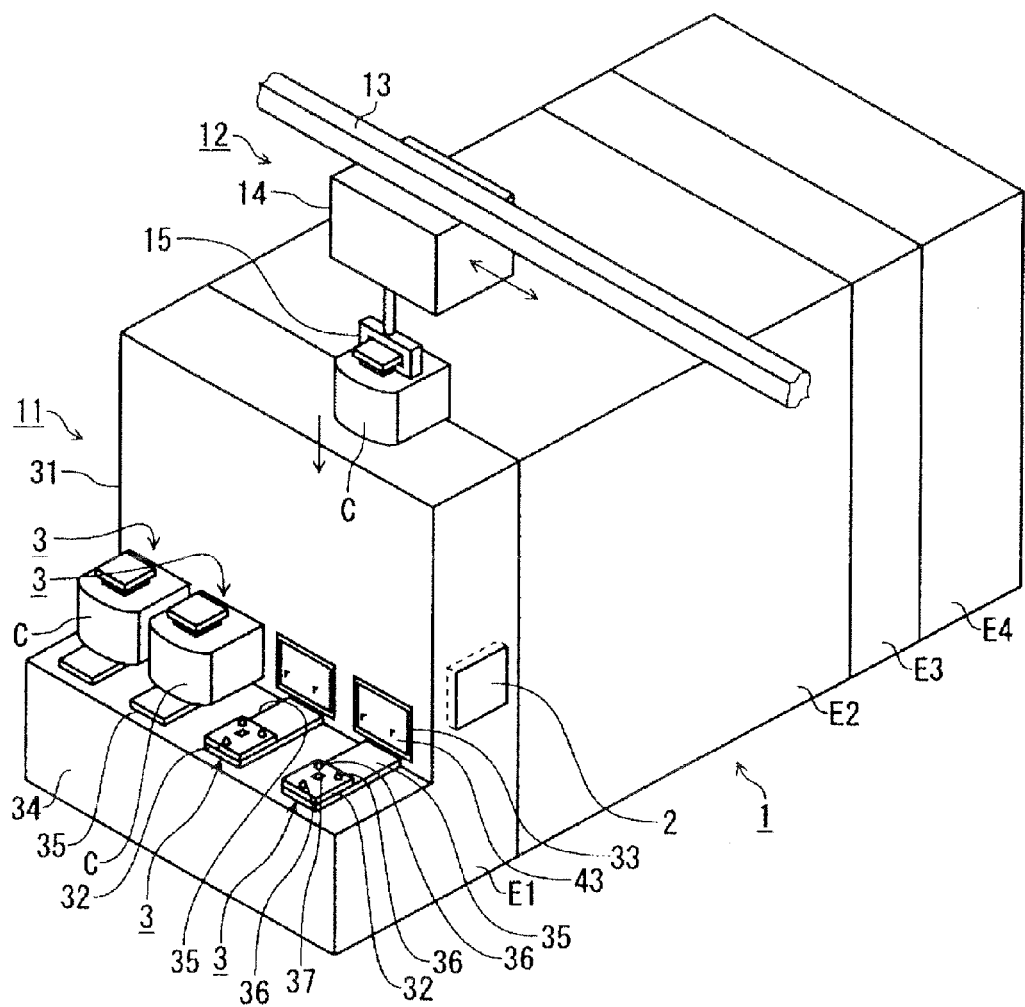
FIG. 1 is perspective view of a coating and developing apparatus that is a substrate processing apparatus to which the present invention is applied.

A coating and developing apparatus 1, which is an example of a substrate processing apparatus according to a first embodiment of the present invention, is described with reference to FIG. 1. FIG. 1 is a perspective view of the coating and developing apparatus 1. The coating and developing apparatus 1 is installed in a clean room of a semiconductor manufacturing factory, and is composed of a carrier block E1, a processing block E2 and an interface block E3 which are connected linearly. An exposure apparatus E4 is connected to the interface block E3 on the opposite side to the processing block E2 side. A space outside of the coating and developing apparatus 1 is a transport area 11 for transporting a carrier C containing wafers W (i.e., substrates). A below-described carrier transport mechanism 12 transports the carrier in the transport area 11. The carrier C is a transport container, which is called "FOUP", for example.

Functions of the respective blocks are briefly described. The carrier block E1 is a block for transferring the carrier C to and from the carrier transport mechanism 12. The carrier block E1 also transfers wafers W between the carrier C having been transported to the carrier block E1, and the processing block E2. The carrier block E1 is described in detail below.

The processing block E2 is a block for performing various liquid processes to the wafers W, such as a resist coating process and a developing process, and a heating process. The exposure apparatus E4 exposes a resist film, which has been formed on each of the wafers W in the processing block E2. The interface block E3 transfers the wafers W between the processing block E2 and the exposure apparatus E4. The wafers W carried out from the carrier C are subjected sequentially to a resist coating process and a heating process in the processing block E2, and are exposed in the exposure apparatus E4. Thereafter, the wafers W are subjected sequentially to a heating process and a developing process, and then are returned to that carrier C.

An apparatus controller 2 that controls operations of the respective units of the coating and developing apparatus 1 is disposed, for example, on a side face of the carrier block E1. The apparatus controller 2 is a computer that transmits control signals to the respective units of the coating and developing apparatus 1. The carrier block E1 is controlled such that, upon receipt of a control signal, wafers W are carried into the below-described carrier block E1 and the wafers W are carried out from the carrier block E1. In addition, the respective blocks E1 to E3 are controlled such that, upon receipt of control signals, wafers W are transported among these blocks and are processed as described above.

The apparatus controller 2 of the coating and developing apparatus 1 is connected to a host computer 20 (not shown in the first embodiment). The apparatus controller 2 is described in detail below. The host computer 20 transmits a control signal to the carrier transport mechanism 12 to thereby control transport of the carrier C in the clean room. The host computer 20 also assigns ID numbers as identification codes to the respective carriers C that are transported in the clean room, and transmits these ID numbers to the apparatus controller 2.

The respective carriers C are transported in the clean room among a plurality of apparatuses including the coating and developing apparatus 1 according to a transporting order set by the host computer 20. The carrier transport mechanism 12 shown in FIG. 1 is described. The carrier transport mechanism 12, which is a so-called overhead hoist transport, includes a moving unit 14 that moves along a track 13 provided on a ceiling of the clean room, and a griping unit 15. The gripping unit 15 moves vertically (moved up and down) relative to the moving unit 14 and grips the carrier C, so that each carrier C can be transported among the plurality of apparatuses.

Figure 2:
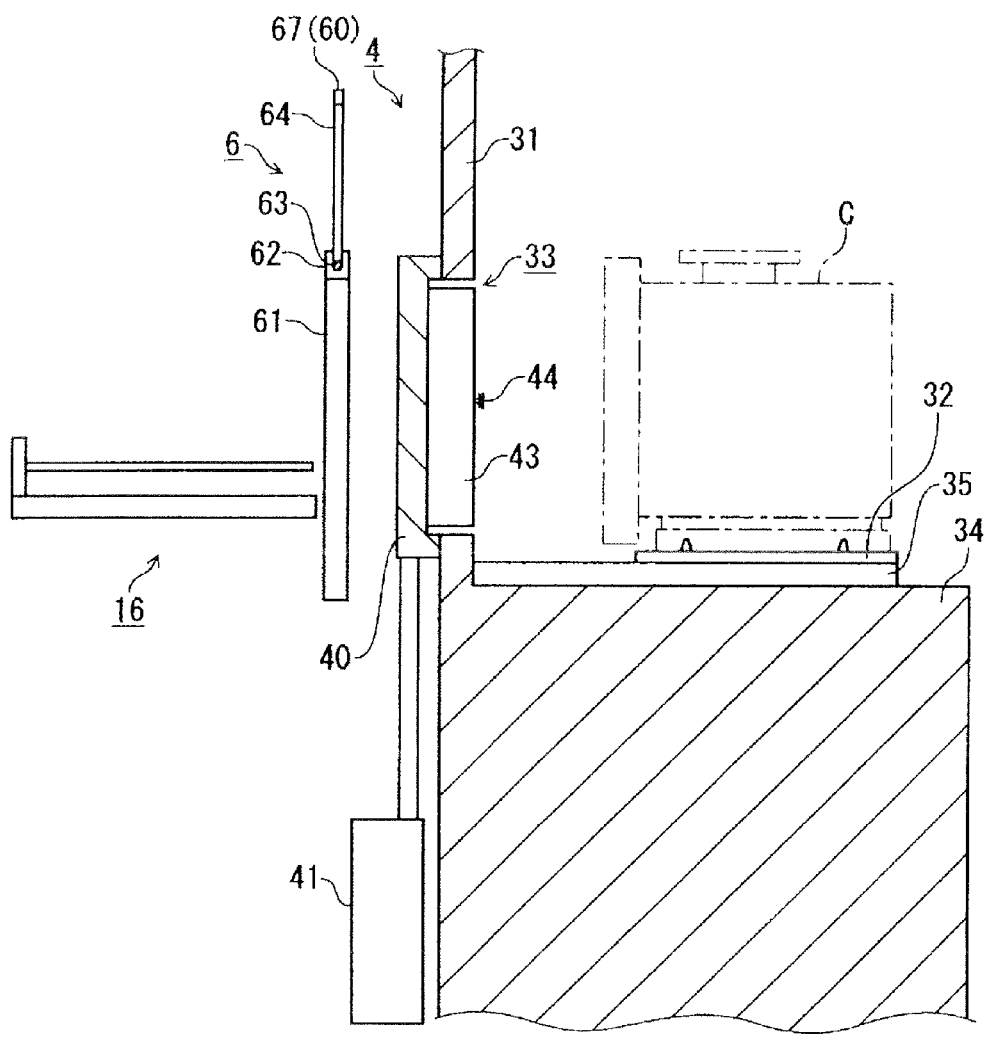
FIG. 2 is a side view of a carrier block of the coating and developing apparatus.

Next, the carrier block E1 is described in detail with reference also to the vertically-sectioned side views of FIGS. 2 and 3. For the convenience of explanation, the side of the carrier block E1 and the side of the interface block E3 are referred to as a rear side and a front side, respectively. The carrier block E1 has a housing 31. The housing 31 constitutes load ports 3, through each of which the carrier C is transferred to and from the carrier transport mechanism 12, and at each of which wafers W are transferred between the carrier C and the inside of the coating and developing apparatus 1.

In addition to the housing 31, each load port 3 includes a stage 32 on which the carrier C can be placed, a transport opening 33 for a wafer W, a door 4 for opening and closing the transport opening 33, and a mapping unit 6. The carrier block E1 is provided with the four load ports 3. A lower part of the housing 31 projects rearward to form a stepped part 34. The stages 32 of the respective load ports 3 are arranged laterally on the stepped part 34. The respective transport openings 33 are formed in a wall of the housing 31 in front of each stage 32.

The stage 32 moves forward and rearward to move the carrier C between a retreated position (unload position) and an advanced position (load position). In FIG. 2, the carrier C located at the unload position is shown by the chain lines. In FIG. 3, the carrier C located at the load position is shown by the solid lines. The carrier C is transported by the carrier transport mechanism 12 to the unload position. At the load position, wafers W are transferred to and from the carrier block E1. The stage 32 is connected to a stage moving mechanism 35. The forward movement and the rearward movement of the stage 32 are performed by the stage moving mechanism 35.

Three pins 36 project upward from a surface of the stage 32. When the carrier C is placed on the stage 32, these pins 36 are inserted and fit into recesses (now shown) formed in a bottom part of the carrier C, so as to prevent displacement of the carrier C on the stage 32. The reference numeral 37 in FIG. 1 depicts a clamp mechanism 37 for fixing the carrier C on the stage 32.

Figure 4:
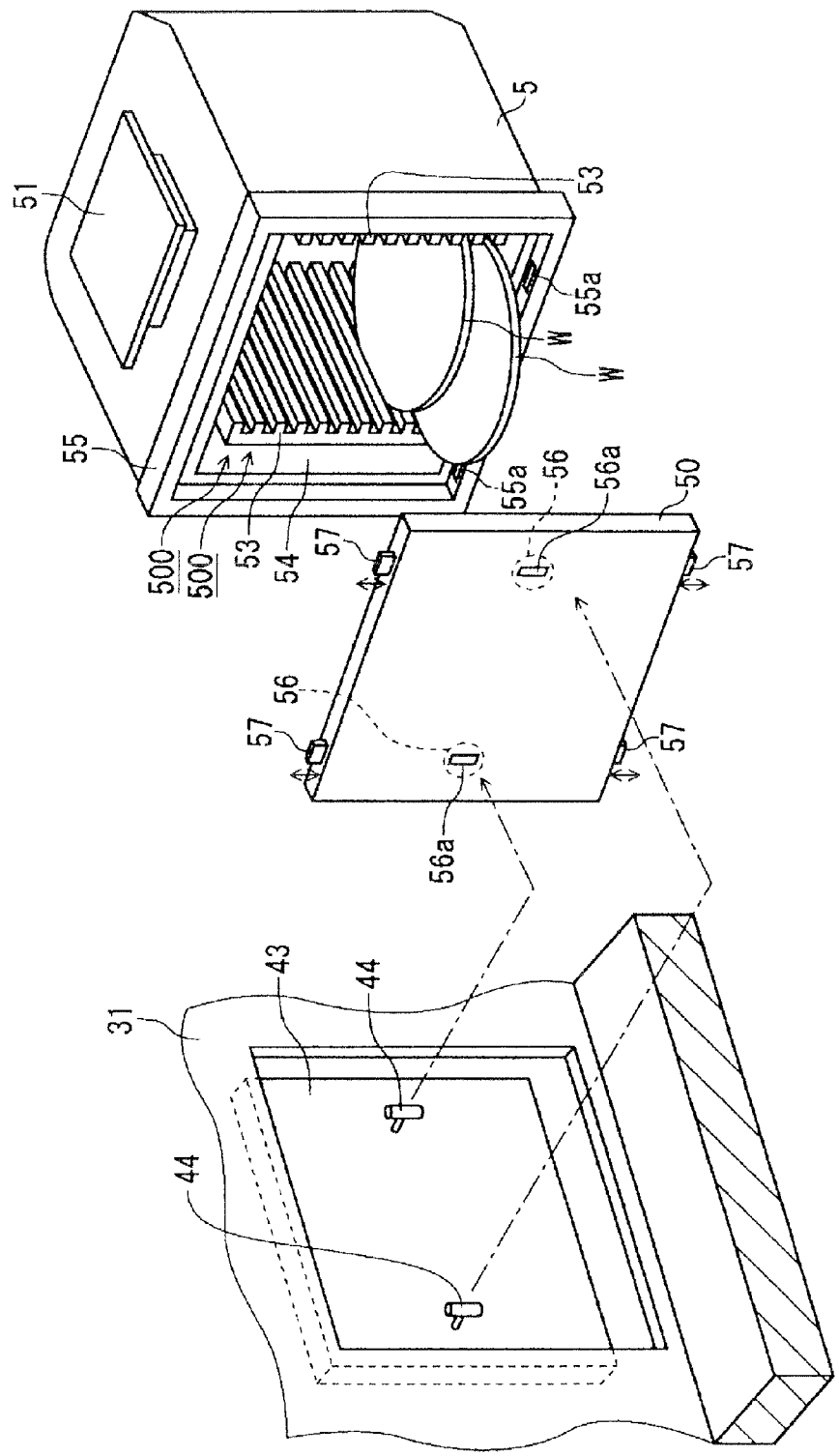
FIG. 4 is a perspective view of a door of the carrier block and a carrier.

The carrier C is described with reference also to FIG. 4. The carrier C is composed of a container main body 5 and a lid 50 detachably attached to the container main body 5. Support members 53 for supporting a peripheral portion of a back surface of a wafer W are formed at multiple levels on the right and left inner sides of the container main body 5. Thus, wafers W are contained in the container main body 5 in a form like shelves. Storage areas for wafers W, which are defined by the support members 53 and an inner wall surface of the container main body 5, are referred to as slots 500. In order to differentiate these slots 500, these slots are sometimes referred to as slot 501, 502, 503 . . . in this order from top to bottom.

A removal opening 54 for wafer W is formed in a front face of the container main body 5. When the removal opening 54 is closed by the lid 50, airtightness of the interior of the container main body 5 is maintained. The reference numeral 55 designates an opening periphery (the periphery of the opening) around the removal opening 54. Engagement grooves 55*a* are formed in an upper part and a lower part of an inner circumferential side of the opening periphery 55 (the upper engagement grooves 55*a* are not shown). A grip portion 51 to be gripped by the aforementioned carrier transport mechanism 12 for transporting the carrier C is provided on the top of the container main body 5.

The lid 50 is described. Right and left rotary members 56 are disposed inside the lid 50. Linear motion members 57 are disposed to extend vertically from the top and bottom of each rotary member 56. Upon rotation of each rotary member 56, the corresponding linear motion members 57 are switched between a condition where ends of the linear motion members 57 project from the upper and lower edge of the lid 50, and a condition where these ends are retracted into the lid 50. When the ends of the linear motion members 57 are engaged with the engagement grooves 55 of the container main body 5, the lid 50 is engaged with the container main body 5 in a locked manner. Formed in each rotary member 56 is a key hole 56*a*, into which a below-described latch key 44 is inserted. Each rotary member 56 is rotated by rotating the corresponding latch key 44 inserted in the key hole 56*a*.

Next, the door 4 is described. The door 4 has a door main body 40 that closes the transport opening 33 from the inside of the housing 31. In FIG. 3, the door main body 40 located at a position to close the transport opening 33 is shown by the solid lines, which position is referred to as closing position. A door opening/closing mechanism 41 is connected to the door main body 40. In order to open the transport opening 33, the door main body 40 is moved by the door opening/closing mechanism 41 from the closing position to a separated position advanced from the closing position. Then, the door main body 40 is moved downward from the separated position by the door opening/closing mechanism 41 to an opening position shown by chain lines in FIG. 3, whereby the transport opening 33 is opened.

Figure 5:
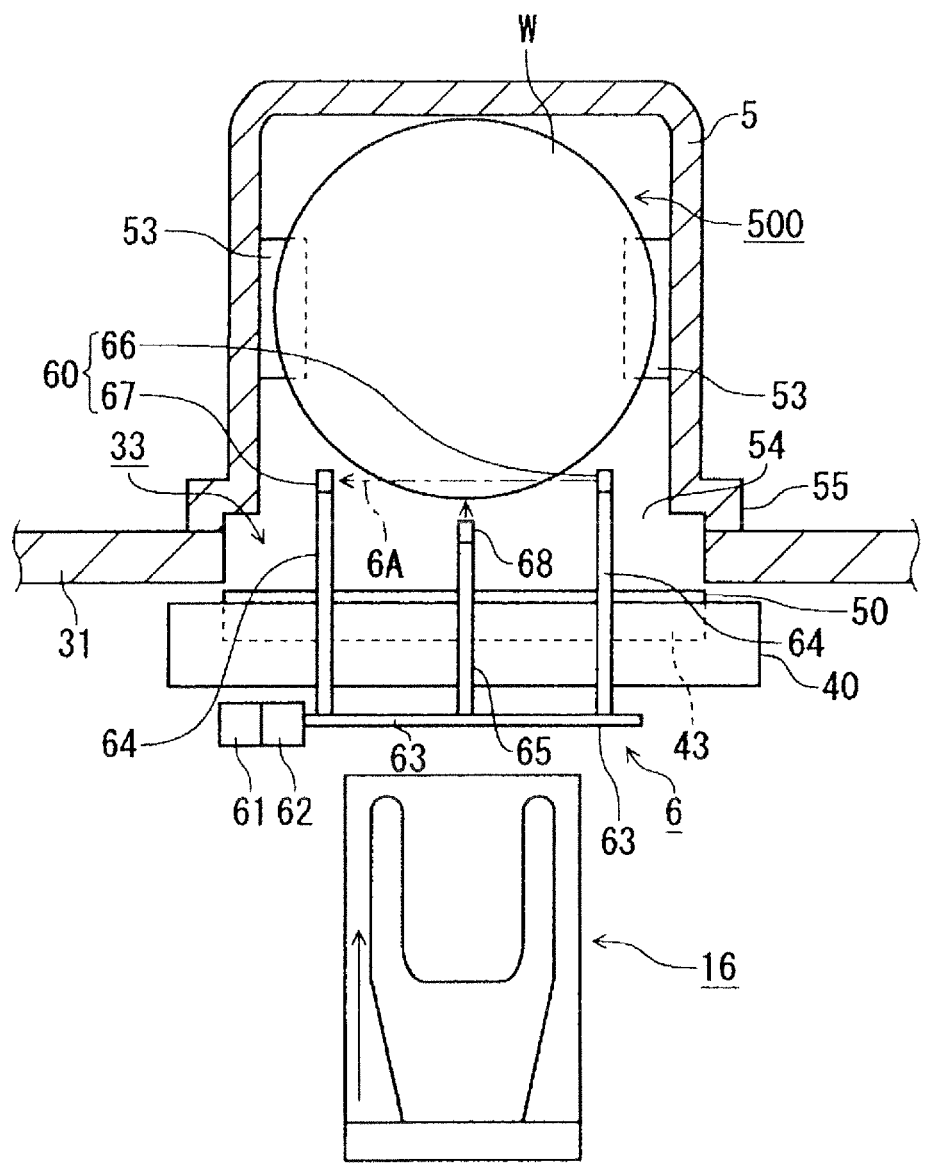
FIG. 5 is a cross-sectional view of the carrier block and the carrier.

As shown in FIG. 5, a transfer mechanism 16, which is shared by the load ports 3, is disposed in the housing 31. The transfer mechanism 16 is configured so as to be vertically movable, movable rightward and leftward, movable forward and rearward, and rotatable about a vertical axis. Due to provision of the transfer mechanism 16, wafers W can be transferred between the carriers C and the processing block E through the opened transport openings 33.

The door 4 is provided, on the rear side of the door main body 40, with a lid opening/closing mechanism 43. The lid opening/closing mechanism 43 has, on its rear side, the latch keys 44. Each latch key 44 can be rotated about a horizontal axis. When the stage 32 moves the carrier C placed on the stage 32 forward and rearward, the latch keys 44 are inserted into and drawn from the key holes 56*a* of the rotary members 56.

Next, the mapping unit 6 is described with reference also to the laterally-sectioned plan view of FIG. 5 showing the carrier C and the carrier block E1. The mapping unit 6 is disposed in the housing 31. The mapping unit 6 is a unit that checks the storage condition of wafers W in the carrier C, which operation is referred to as "mapping". In the coating and developing apparatus 1, the mapping is performed at a timing before wafers W, which have not been processed in the coating and developing apparatus 1, are carried out (removed) from the carrier C, and at a timing after processed wafers W are carried into the carrier C (the details are described later). The mapping unit 6 includes an elevation mechanism 61, a rotation mechanism 62, a support shaft 63, support arms 64, 64, 65, a light emitting device 66, a light receiving device 67 and a reflection sensor 68.

The rotation mechanism 62 is raised and lowered by the elevation mechanism 61. The rotation mechanism 62 is provided with the support shaft 63 which extends laterally. The support shaft 63 is configured to be rotatable about its axis by the rotation mechanism 62. The support arms 64, 65, 64 are disposed on the support shaft 63 at intervals in this order from the left to the right. The support arms 64, 64, 65 extend in parallel with each other perpendicularly to the support shaft 63. The light emitting device 66 and the light receiving device 67, which are paired to constitute a transmission sensor, are disposed on the distal ends of the respective support arms 64. The light emitting device 66 and the light receiving device 67 may be also referred to as "sensor pair 60." The reflection sensor 68 is disposed on the distal end of the support arm 65. The reflection sensor 68 and the sensor pair 60, which constitute a detecting unit, are located at the same height level.

Figure 3:
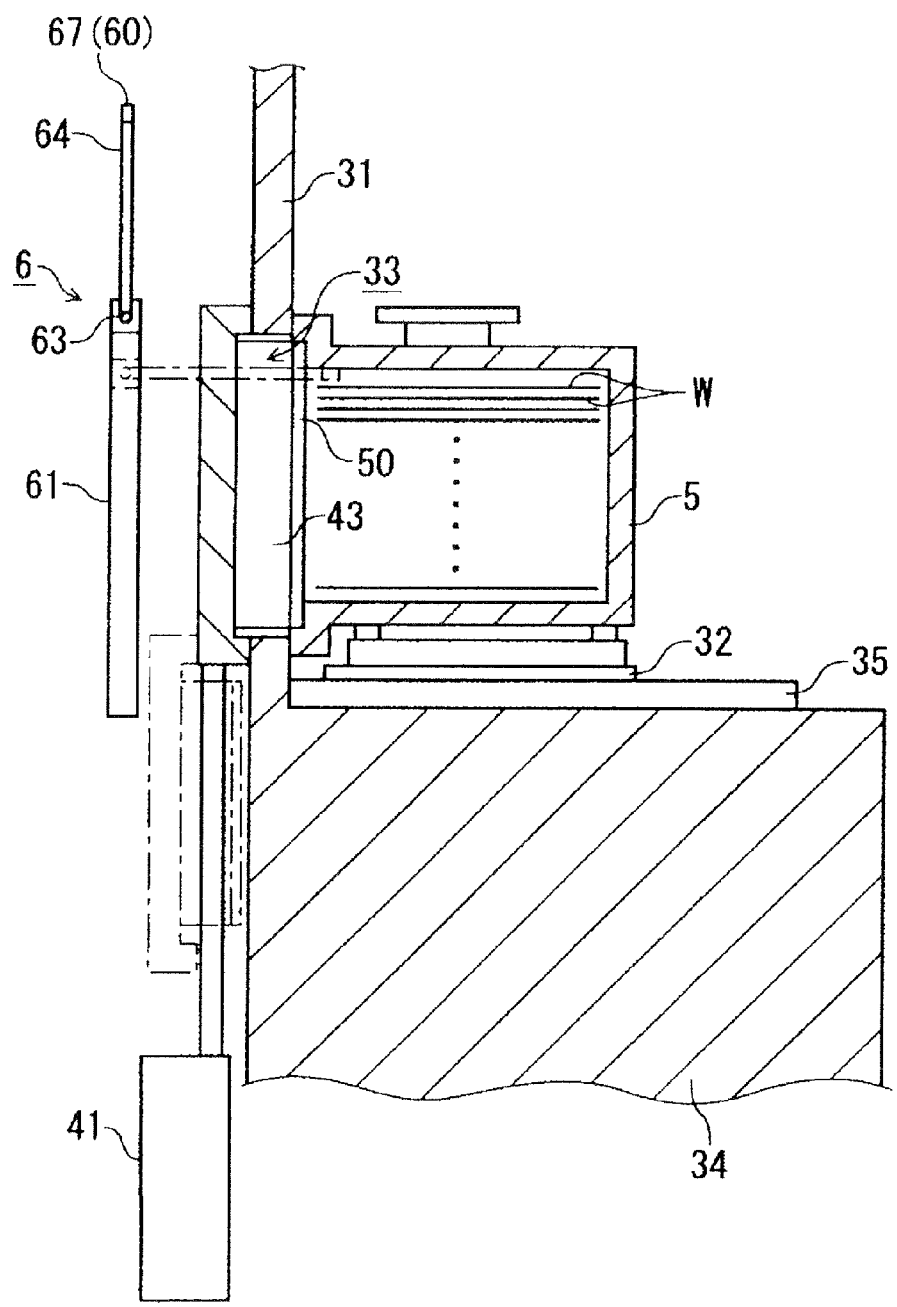
FIG. 3 is a side view of the carrier block of the coating and developing apparatus.

When the mapping is not performed, the support arms 64, 64, 65 take an upright posture for standby as shown by the solid lines in FIG. 3. Positions of the sensor pair 60 and the reflection sensor 68 supported by the support arms 64, 64, 65 for standby are referred to as sensor standby positions. When the mapping is performed, the support arms 64, 64, 65 take a horizontal posture. At this time, from the sensor standby positions, the sensor pair 60 goes into the container main body 5 from which the lid 50 has been removed, as shown in FIG. 5, through combination of the elevation movement of the elevation mechanism 61 and the rotation movement by the rotation mechanism 62.

In FIG. 5, a light axis of a light, which travels from the light emitting device 66 toward the light receiving device 67 when the mapping is being performed, is shown by the chain line arrow indicated by the reference numeral 6A. The sensor pair 60 is disposed on the support arms 64 such that the light axis 6A overlaps with each wafer W in the container main body 5. In addition, the reflection sensor 68 is disposed on the support arm 65 to be located in front of the light axis 6A when the mapping is being performed. The reflection sensor 68 emits light rearward (toward the container main body 5). When the light falls on a wafer W, the light is reflected by the wafer W so that the reflected light enters the reflection sensor 68. When the light receiving device 67 receives the light of the light axis 6A and the reflection sensor 68 receives the reflected light, respectively, detection signals informing the receipt of the lights are transmitted to the apparatus controller 2.

Figure 6:
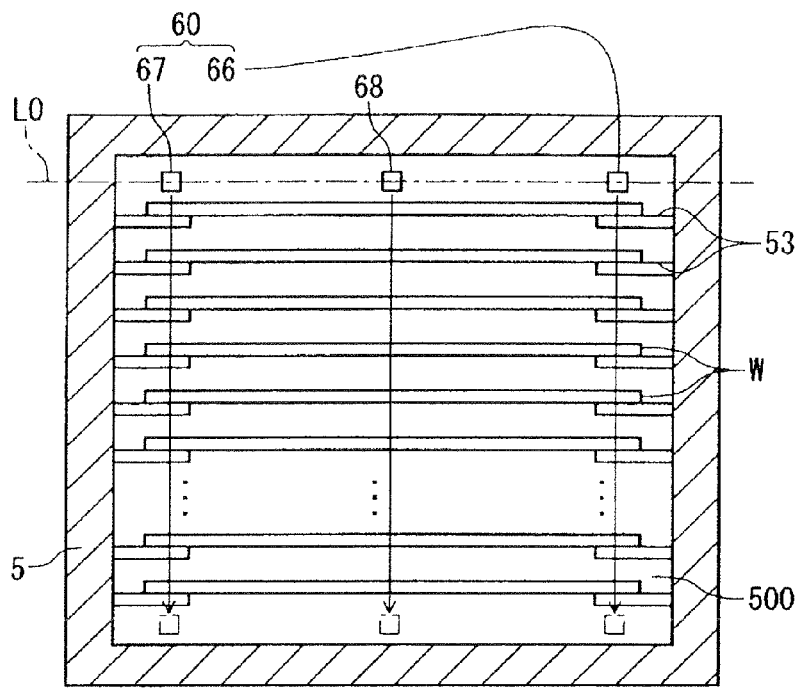
FIG. 6 is a vertically-sectioned front view of the carrier.

FIG. 6 shows a transversely-sectioned side view of the carrier C together with the sensor pair 60 and the reflection sensor 68. When the mapping is started, the sensor pair 60 and the reflection sensor 68 are located on mapping start positions (positions shown by the solid lines in FIG. 6) above the uppermost support member 53. Then, the light axis 6A is formed by the sensor pair 60, and light is emitted rearward from the reflection sensor 68. Then, the sensor pair 60 and the reflection sensor 68 move at a constant speed toward mapping end positions (positions shown by the chain lines in FIG. 6) below the lowermost slot 500. During the movement, upon receipt of lights by the light receiving device 67 of the sensor pair 60 and by the reflection sensor 68, the light receiving device 67 and the reflection sensor 68 respectively output detection signals to the apparatus controller 2.

Based on the detection signals from the sensor pair 60 and the reflection sensors 68, the apparatus controller 2 obtains, as mapping data, information on the height position of a wafer W in each slot 500 and information on whether or not a wafer W is stored in each slot 500. The height position of a wafer W is defined by the distance from a reference position L0, which is shown by the horizontal chain lines in FIG. 6, to the upper end of the wafer W.

Figure 7:
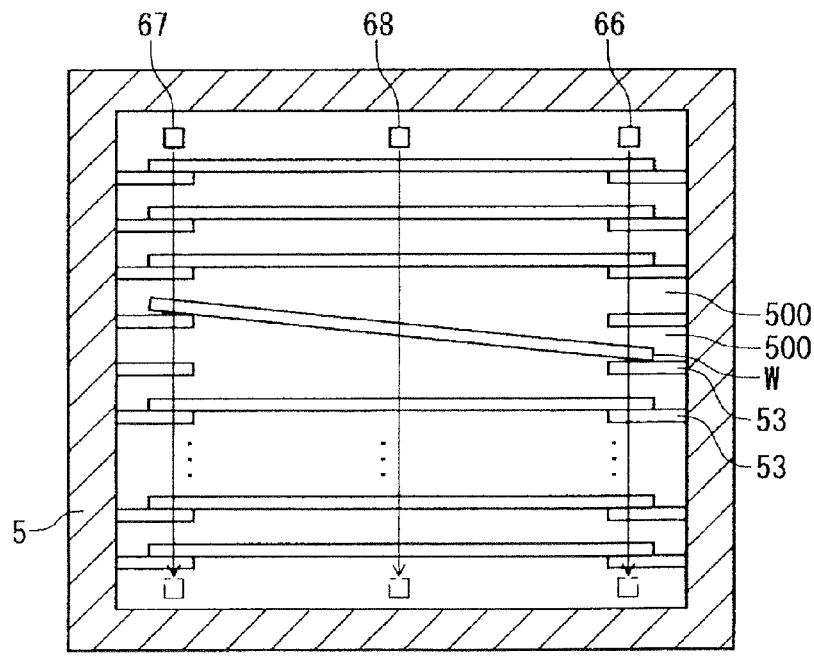
FIG. 7 is a vertically-sectioned front view of the carrier.

In addition, the thickness of a wafer W is obtained as the mapping data. Erroneous transport of wafer(s) W may result in a case where one wafer W is contained across slots 500 in an inclined posture (Case 1) as shown in FIG. 7, and in a case where two or more wafers W are contained in one or more slots 500 with the wafers W lying on top of one another (Case 2). The case where two or more wafers W are stored in two or more slots 500 means a case where one or more wafer lies on the wafer W in the inclined posture as shown in FIG. 7.

It is assumed that the apparatus controller 2 detects the thickness of the wafer W based only on the data obtained from the sensor pair 60. Under such an assumption, since the time period during which the light axis 6A is blocked in the above Cases 1 and 2 is longer than a case in which one wafer W is contained in one slot 500, the detected thickness of the wafer W must be abnormal values in the both cases. However, the mapping unit 6 includes the reflection sensor 68 in addition to the sensor pair 60. Since the wafers W lie on the top of one another in the Case 2, the time period during which the reflection sensor 68 receives light is longer than the Case 1.

In this manner, the apparatus controller 2 detects the thickness of a wafer W based on data obtained from the sensor pair 60 and the reflection sensor 68. If the detected thickness exceeds a threshold value, it is regarded that Case 2 occurs. Namely, the Cases 1 and 2 can be distinguished from each other by the apparatus controller 2. Wafers W whose storage condition is judged to correspond to the Case 2 at the mapping performed when wafers W are carried into the apparatus (hereinafter referred to simply as "carry-in mapping") will not be carried into the coating and developing apparatus 1. On the other hand, the transport operation is controlled such that a wafer W whose storage condition is judged to correspond to the Case 1 will be carried into the coating and developing apparatus 1.

Figure 8:
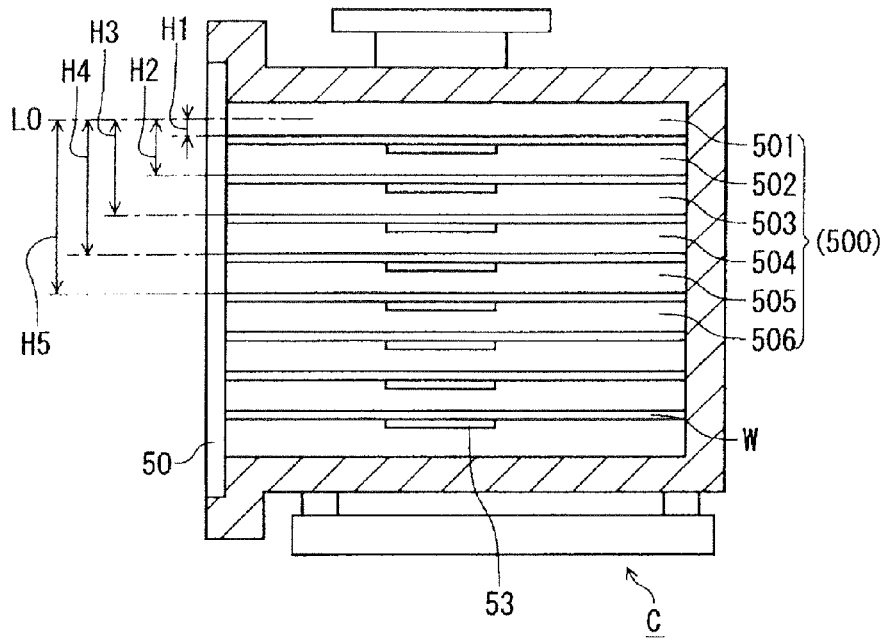
FIG. 8 is a vertically-sectioned side view of the carrier.

As previously described in the "Background Art" part, the carrier C is manufactured so as to conform to a predetermined standard, an explanation for which is made with reference to FIG. 8. The carrier C is constructed such that each one of wafers W is horizontally stored in respective ones of the slots 500, and that the height position of each slot 500 (501, 502, 503 . . . ) relative to the reference position L0 is included in a predetermined allowable range. Thus, the height positions H1, H2, H3 . . . of the wafers W in the respective slots 501, 502, 503 . . . should be included in the respective allowable ranges which are set for the corresponding wafers W.

Figure 9:
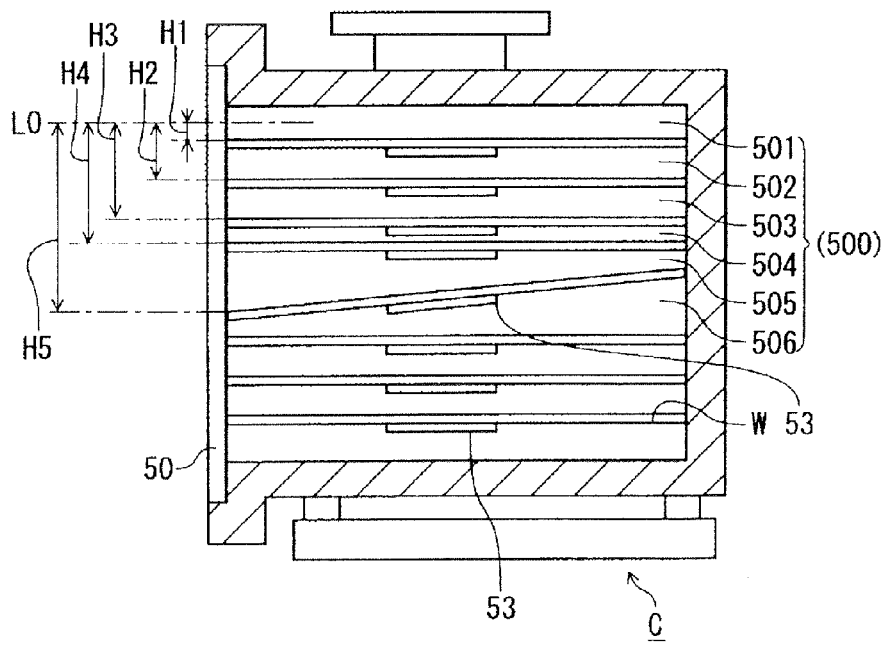
FIG. 9 is a vertically-sectioned side view of the carrier.

However, due to manufacturing error of the carrier C, the position of the support member 53 may be shifted in the vertical direction, so that the height position of the slot 500 deviates from the allowable range which is set therefor. For example, FIG. 9 shows an example in which the height position of the slot 503 is shifted downward to deviate from the allowable range. In addition, due to manufacturing error, the support member 53 may be made such that it obliquely supports a wafer W, so that the height position of the slot 500 deviates from the allowable range. For example, in the example shown in FIG. 9, the support member 53 of the slot 505 is constructed in this manner, whereby the wafer W is supported such that the lid 50 side of the wafer W is lowered. That is, the height position of the slot 505 is lowered so as to deviate from the allowable range.

The transfer mechanism 16 can adjust its height position when it enters the carrier C in order to remove a wafer W from each slot 500, based on the height positions H1, H2, H3 . . . of the wafers W obtained by the carry-in mapping.

However, if the height position of the slot 500 deviates from the allowable range as described above, the transfer mechanism 16 may rub and damage the back surface of a wafer W during removal of the wafer W. In detail, in the example shown in FIG. 9, since the height position of the slot 503 is shifted downward, when the transfer mechanism 16 transports the wafer W in the slot 503, the transfer mechanism 16 enters the carrier C in such a manner that the transfer mechanism 16 does not come into contact with the front surface of the wafer W in the slot 504. However, at this time, since a clearance between the back surface of the wafer W in the slot 503 and the transfer mechanism 16 is narrow, the transfer mechanism 16 comes into contact with the wafer W in the slot 503 to damage the back surface of the wafer W. Besides, since the wafer W in the slot 505 is supported such that the lid side of the wafer W is lowered, when the transfer mechanism 16 transports the wafer W in the slot 505 in such a manner that the transfer mechanism 16 does not come into contact with the front surface of the wafer W in the slot 506, the transfer mechanism 16 damages the lid 50 side of the back surface of the wafer W in the slot 505.

Thus, it is disadvantageous to continuously use the carrier C having the slot 500 whose height position deviates from the allowable range. Thus, in the first embodiment, in addition to the carry-in mapping, a mapping is again performed when wafers W are returned to the carrier C. This mapping is referred to as "carry-out mapping". The apparatus controller 2 judges whether the carrier C has an abnormality or not, based on the height positions of the wafers W obtained both by the carry-in mapping and the carry-out mapping.

An explanation is be made for the reason why an abnormality of the carrier C can be judged based on the height positions of the wafers obtained by both the carry-in mapping and the carry-out mapping. At the carrying-in of the carrier C, there is a possibility that the mapping is performed with a wafer W being contained in an inclined manner because of troubles in transporting of the carrier C or in removing of the lid 50. In addition, there is a possibility that the mapping is performed with a wafer W being contained in an inclined manner in the slot 500 because of an erroneous operation of the transfer mechanism 16.

However, if both height positions of the same wafer in a certain one slot 500 obtained by the carry-in mapping and the carry-out mapping deviate from the allowable range, and if the height position of the wafer in the certain slot 500 obtained by the carry-in mapping and that obtained by the carry-out mapping are substantially the same, the thus obtained abnormal height positions of the wafer W at the carry-in mapping and the carry-out mapping are highly possibly caused by the defect of the carrier C itself. Thus, it is judged that the height position of the one slot 500 in the carrier C is abnormal, in other words, the carrier C is judged as an abnormal carrier C. Generally speaking, when the height position of the same slot 500 is judged to be abnormal both in the carry-in mapping and the carry-out mapping, it is judged that the carrier C has an abnormality. The abnormality judgment is performed for each slot 500.

In addition, as described later, it is judged whether or not the transfer mechanism 16 has an abnormality based on height positions of wafers obtained by the carry-in mapping and the carry-out mapping. Moreover, as also described later, based on the height positions of a wafer W, it is judged whether or not inclination of the wafer W occurs when the carrier C is transported from a preceding apparatus of the coating and developing apparatus 1 to the load port of the coating and developing apparatus 1, or when the lid 50 is removed from the carrier C. This judgment is referred to as "in-loading abnormal judgment".

When a carrier C is judged to have an abnormality, the apparatus controller 2 transmits, to the host computer 20, the ID number of the carrier C and the number of the abnormal slot 500. The host computer 20 gives an instruction to another apparatus to stop transporting of the wafer W in the slot 500, for example. The other apparatus is an apparatus to which the abnormal carrier C is to be transported next to the coating and developing apparatus 1. Then, when a series of predetermined processes to be performed in the clean room to wafers W stored in the abnormal carrier C have been completed, the abnormal carrier C is placed on a predetermined placement position in the clean room by the carrier transport mechanism 12. Based on the judgment, a user excludes the carrier C having an abnormality from the placement position.

Next, the apparatus controller 2 is described with reference FIG. 10. The apparatus controller 2 includes a program storage unit 21, a CPU 22 and a memory 23, which are connected to a bus 24. The mapping unit 6 is also connected to the bus 24, so that detection signals of the sensor pair 60 and the reflection sensor 68 are outputted to the apparatus controller 2. The program storage unit 21 is formed of a computer storage medium such as a flexible disc, a compact disc, a hard disc, an MO (magneto optic disc), a memory card, etc. A program 25 stored in the storage medium is installed to the apparatus controller 2.

The program 25 includes instructions (respective steps) such that control signals are transmitted to respective units of the coating and developing apparatus 1 to control their operations, whereby transport of wafers W, processes of the wafers W in the respective blocks E1 to E3, carrying out of the wafers W from the carrier C and carrying in of the wafers W to the carrier C can be performed. The CPU 22 executes various computing operations for outputting control signals.

Figure 10:
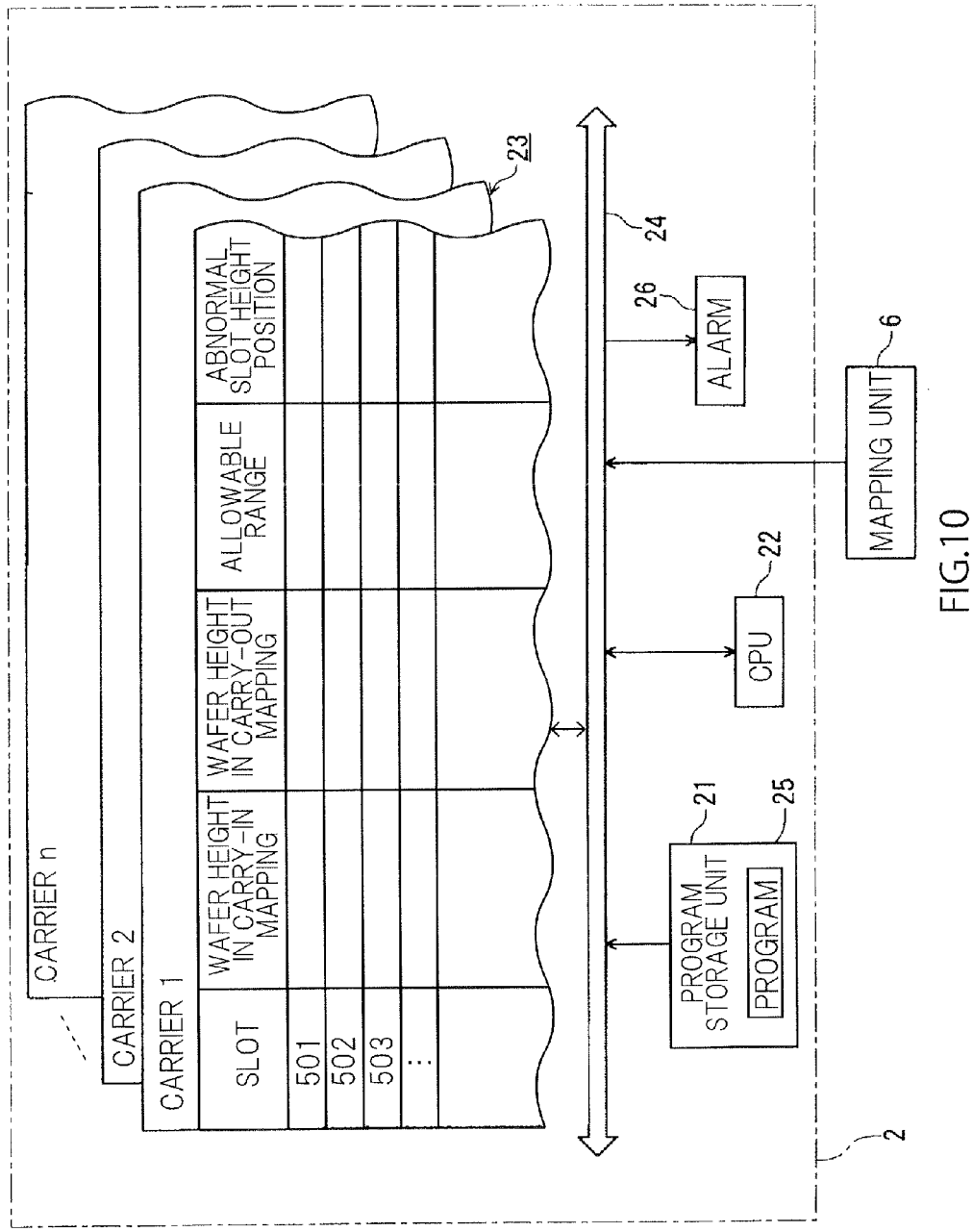
FIG. 10 is a block diagram showing the configuration of an apparatus controller.

As schematically shown in FIG. 10, the memory 23 stores the ID numbers (identification information) of the carriers C. In the illustrated example, the ID numbers are expressed by "1" to "n" ("n" is a natural number). Mapping data obtained by the carry-in mapping the carry-out mapping are stored for each ID number.

The carry-in mapping data include: the height position of a wafer W in each slot 500, presence or absence of a wafer W in each slot 500, the thickness of each wafer W, and presence or absence of wafers W lying on the top of one another (detected based on the thickness). Among the above data, only the height positions of wafers W, which are used for judging whether or not the carrier C has an abnormality, are shown in FIG. 10, as the data to be stored in the memory 23. The carry-out mapping data includes the height positions of wafers W. For each ID number, the memory 23 stores judgment results on presence or absence of abnormality of the height positions of the slots, which judgment results have been obtained based on the height positions of the wafers W at the carry-in mapping and the carry-out mapping. The memory 23 also stores the allowable range of the height position of the wafer W in each slot, which is set for each slot for the purpose of the judgment.

An alarm output unit 26 is connected to the bus 24. When the height position of a slot is judged to have an abnormality, the alarm output unit 26 informs a user of the ID number of the corresponding carrier C and the number of the slot judged to have the abnormality, by displaying them on a screen or by outputting them phonetically. Similarly, when the transfer mechanism 16 is judged to have an abnormality, the alarm output unit 26 outputs an alarm informing the fact.

In addition, when it is judged in the in-loading abnormal judgment that an abnormality occurs, the alarm output unit 26 outputs an alarm informing the fact.

With reference to FIGS. 11 to 16, explanations are made for the loading process that carries the carrier C into the coating and developing apparatus 1 and carries wafers W in the carrier C into the apparatus, and for the unloading process that returns the wafers W from the coating and developing apparatus 1 into the carrier C and carries out the carrier C from the stage 32.

Figure 11:
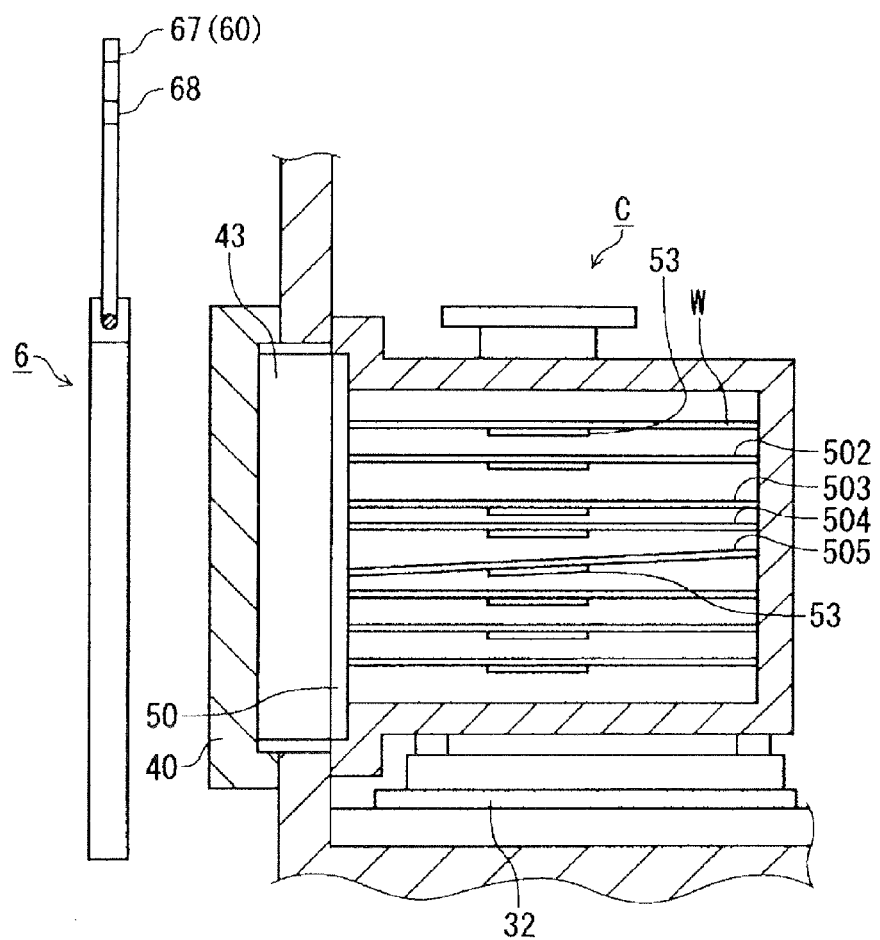
FIG. 11 is an explanatory drawing showing wafer transfer between the carrier block and the carrier.
Figure 12:
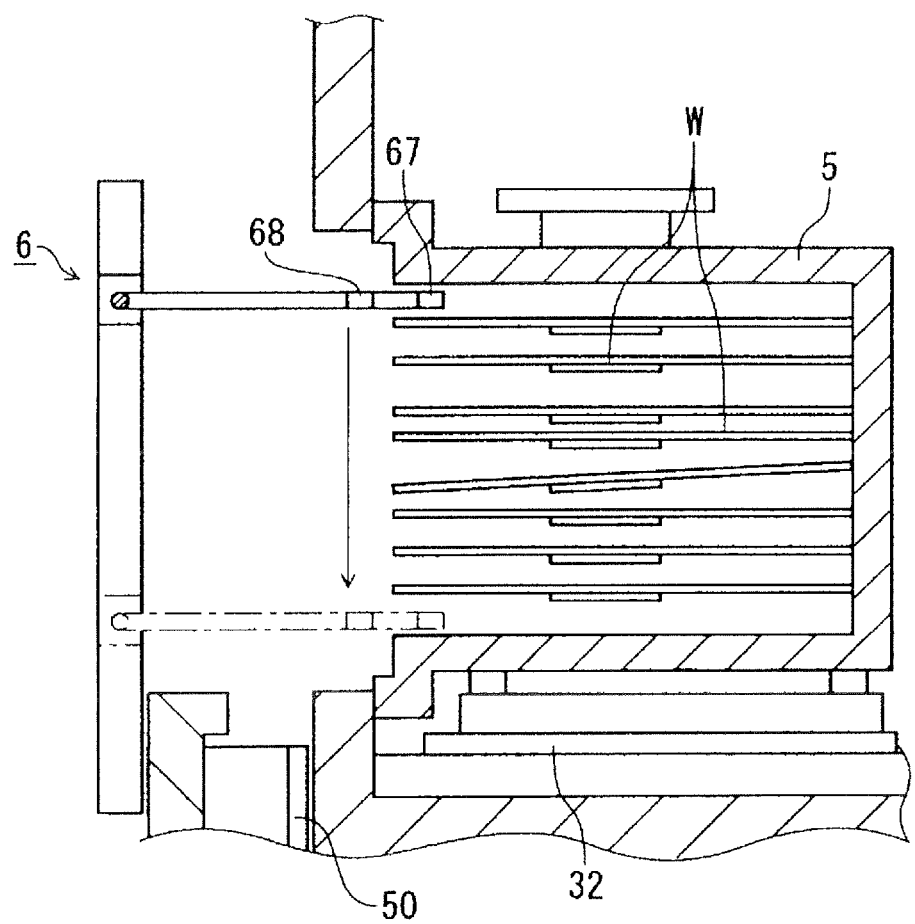
FIG. 12 is an explanatory drawing showing the wafer transfer between the carrier block and the carrier.

The ID number of the carrier C to be transported to the coating and developing apparatus 1 is transmitted from the host computer 20 to the apparatus controller 2 of the coating and developing apparatus 1. Thereafter, the carrier C is transported by the carrier transport mechanism 12 from the preceding apparatus to the coating and developing apparatus 1. The carrier C is placed on the stage 32 and is located on the unload position. After that, as shown in FIG. 11, the carrier C is moved to the load position. The opening periphery 55 of the carrier C is pressed against the housing 31, and the latch keys 44 are inserted into the key holes 56a of the rotary members 56. Described herein is a case where the carrier C having the abnormal slots 503 and 505, which has been described with reference to FIG. 9, is transported to the stage 32.

The latch key 44 is rotated to disengage the lid 50 from the container main body 5. Following thereto, the door main body 40 is moved forward and then downward to the opening position, whereby the transport opening 33 is opened. By combining the elevation movement of the rotation mechanism 62 by the elevation mechanism 61 of the mapping unit 6 with the rotation of the support shaft 63, the sensor pair 60 and the reflection sensor 68 are moved from the sensor standby positions to the mapping start positions shown by the solid lines in FIG. 12. Then, as described with reference to FIG. 5, the carry-in mapping is started. Namely, the sensor pair 60 and the reflection sensor 68 are moved downward to the mapping end positions shown by the chain lines in FIG. 12, while light is emitted from the light emitting device 66 of the sensor pair 60 and the reflection light 68. When the sensor pair 60 and the reflection sensor 68 reaches the mapping end positions, the light emission from the light emitting device 66 and the reflection sensor 68 is stopped so that the carry-in mapping is finished. After that, the sensor pair 60 and the reflection sensor 68 are returned to their standby positions.

Figure 13:
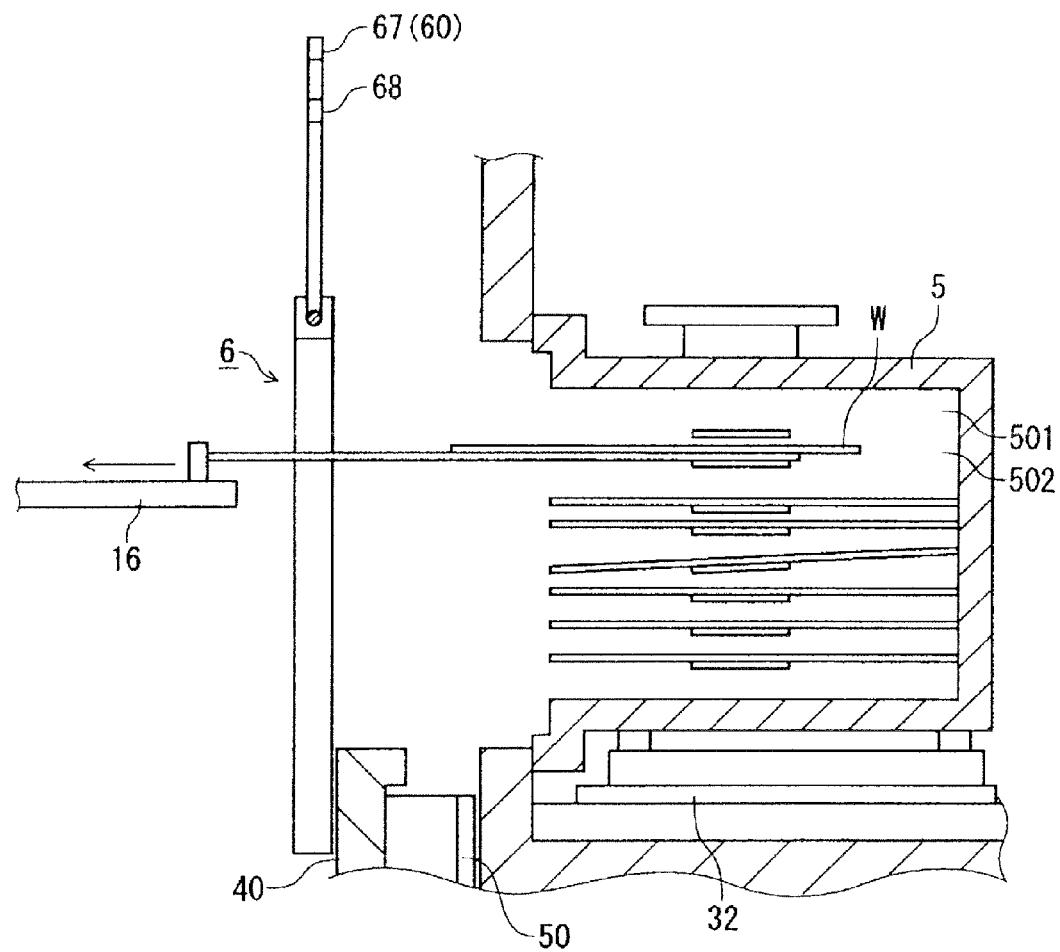
FIG. 13 is an explanatory drawing showing the wafer transfer between the carrier block and the carrier.

Based on the detection signals outputted from the reflection sensor 68 and the light receiving device 67, the apparatus controller 2 obtains data on whether presence or absence of the wafer W in each slot 500, the thickness of the wafer W (in other words, presence or absence of wafers W lying on the top of one another), and the height position of the wafer W in each slot. From each of the slots 500 that are judged to contain the wafer W (but failing to contain the wafers W lying on the top of one another), the wafers W are carried out from the slots by the transfer mechanism 16 and delivered to the processing block E2 (FIG. 13). The wafers W are transported one by one, starting from the uppermost slot (i.e., the slot 501).

Figure 14:
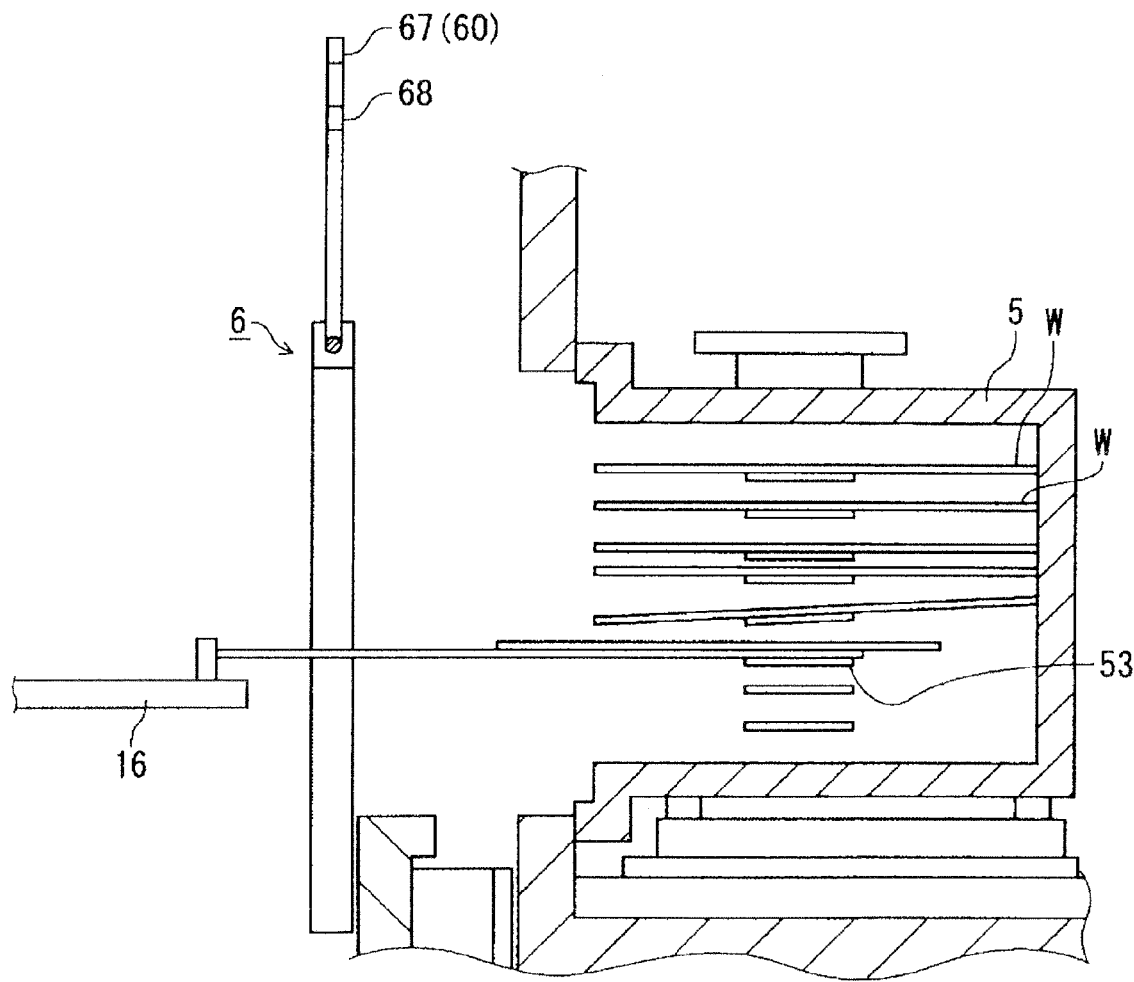
FIG. 14 is an explanatory drawing showing the wafer transfer between the carrier block and the carrier.
Figure 15:
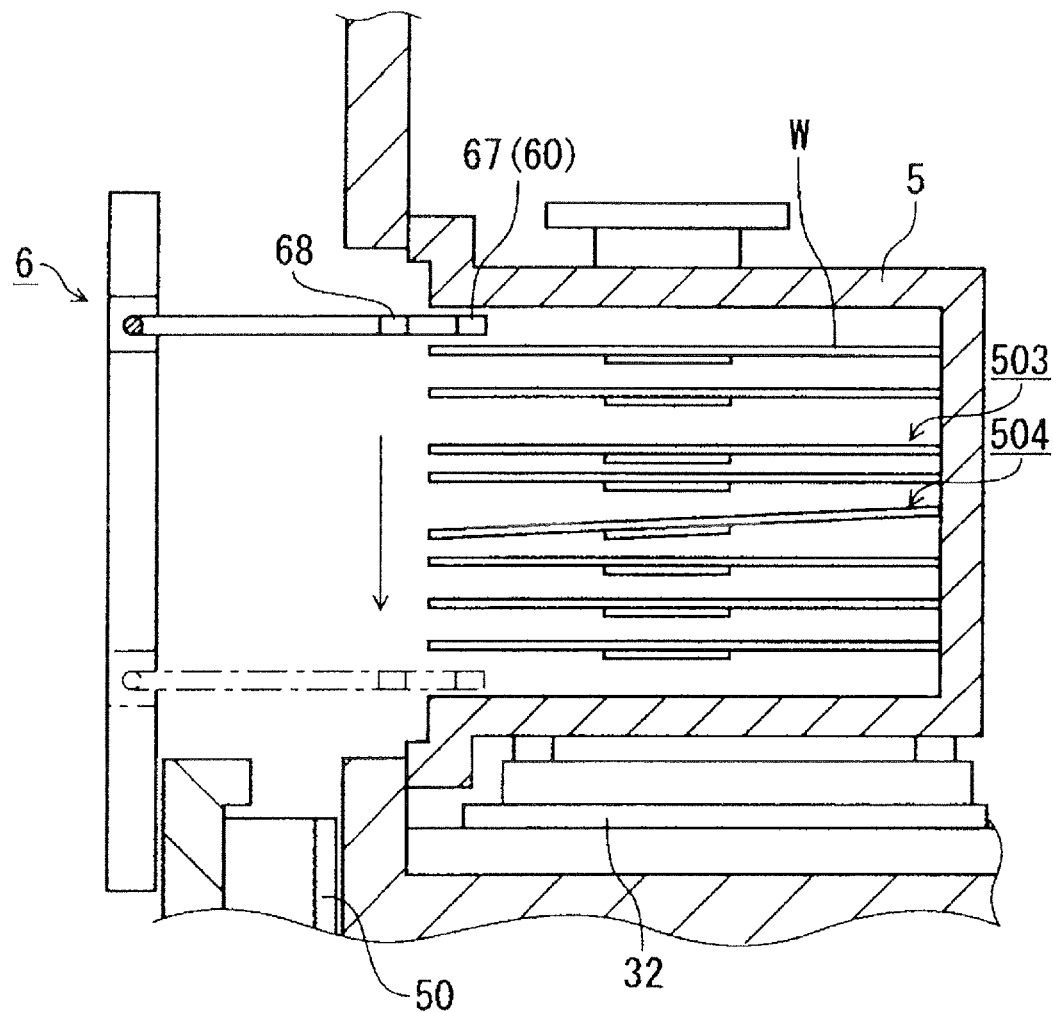
FIG. 15 is an explanatory drawing showing the wafer transfer between the carrier block and the carrier.

Thereafter, the wafers W, which have been transported through the blocks E2 and E3 by the transfer mechanism 16 and processed in the blocks E2 and E3, are sequentially returned to the carrier C to be stored in the slots 500 where these wafers W was originally stored (FIG. 14). After all the processed wafers W have been returned to the carrier C, the sensor pair 60 and the reflection sensor 68 are moved from the standby positions to the mapping start positions. Then, the carry-out mapping is started (FIG. 15). Namely, the sensor pair 60 and the reflection sensor 68 are moved downward, while light is emitted from the light emitting device 66 of the sensor pair 60 and the reflection light 68. When the sensor pair 60 and the reflection sensor 68 have reach the mapping end positions, the light emission from the light emitting device 66 and the reflection sensor 68 is stopped so that the carry-out mapping is finished. After that, the sensor pair 60 and the reflection sensor 68 are returned to the standby positions.

Based on the detection signals outputted from the reflection sensor 68 and the light receiving device 67, the apparatus controller 2 obtains the height position of the wafer W in each slot 500. Then, it is judged for each slot 500 whether or not the height positions of the wafer W obtained by both of the carry-in mapping and the carry-out mapping deviate from the allowable range. If it is judged for a certain slot 500 that height positions of the wafer W obtained by the carry-in mapping and the carry-out mapping both deviate from the allowable range, the difference between these height positions is calculated, and then it is judged whether or not the difference exceeds a threshold value. If the difference is not greater than the threshold value, in other words, if the height positions of the wafer W are close to each other, it is judged that the height position of the slot 500 is abnormal. The judgment result is outputted together with the ID number of the carrier C, as an alarm. In the example shown in FIG. 15, since the slots 503 and 505 each have an abnormality, an alarm informing that the slots 503 and 505 are judged to have an abnormality and the ID number of the corresponding carrier C is outputted.

Figure 16:
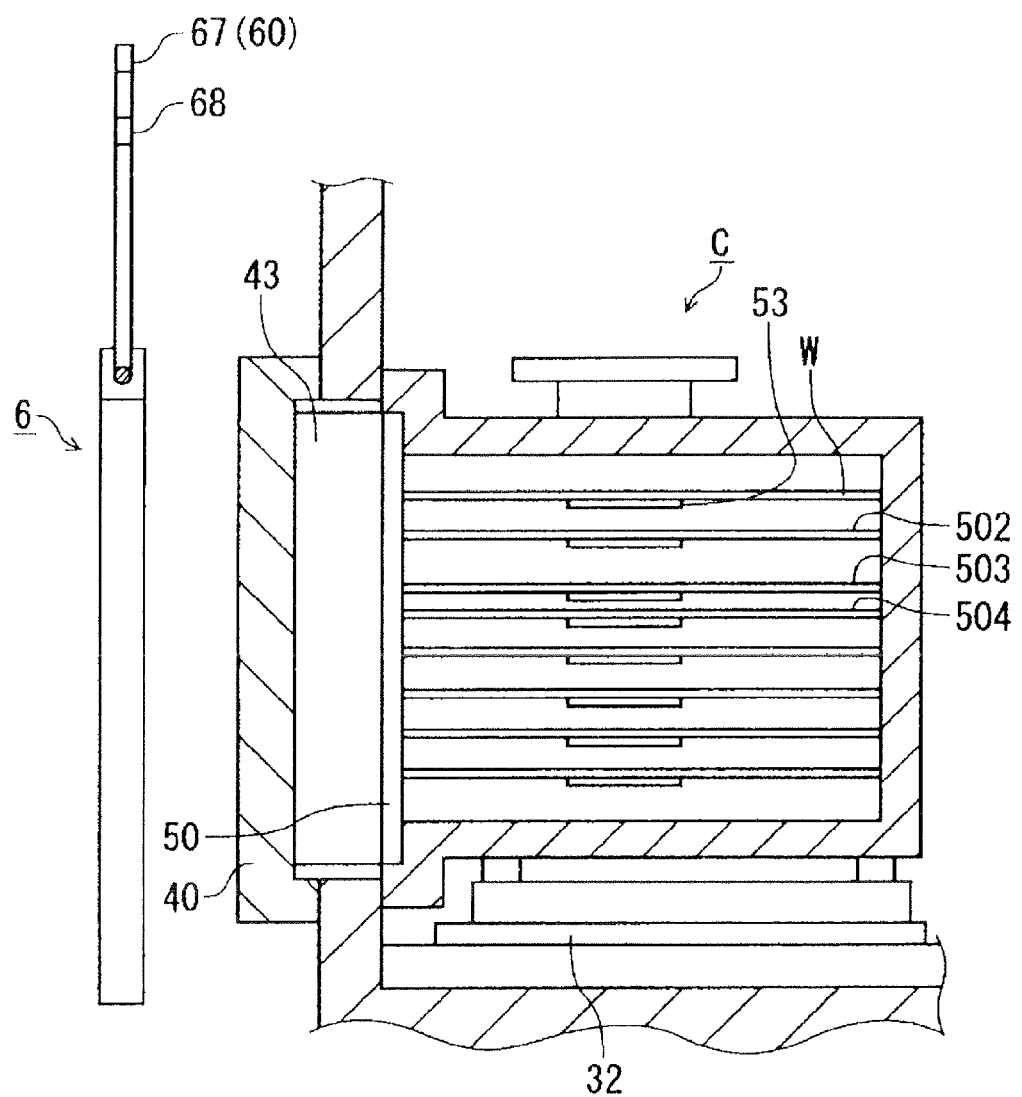
FIG. 16 is an explanatory drawing showing the wafer transfer between the carrier block and the carrier.

After that, the door main body 40 is moved to the closing position to close the transport opening 33, and the lid 50 is pressed against the container main body 5. The latch keys 44 are rotated to engage the lid 50 and the container main body 5 with each other. The lid 50 held by the lid opening/closing mechanism 43 is released, and the lid opening/closing mechanism 43 is returned to the standby position (FIG. 16). Thereafter, the carrier C is moved to the unload position. Then, the carrier C is transported by the carrier transport mechanism to another apparatus. After that, the carrier C is transported between the apparatuses as described above, and is then transported to the predetermined placement position. Thereafter, the carrier C is excluded from the placement position by a user of the apparatus.

Figure 17:
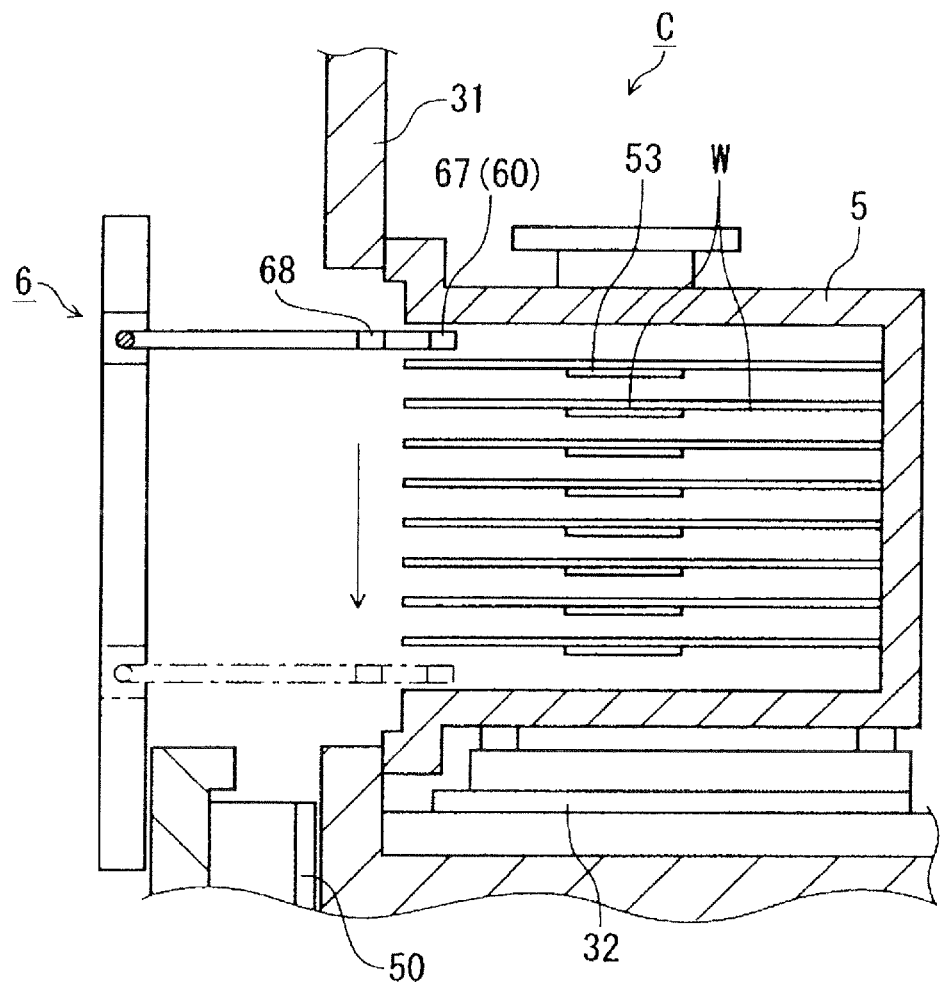
FIG. 17 is an explanatory drawing showing the wafer transfer between the carrier block and the carrier.
Figure 18:
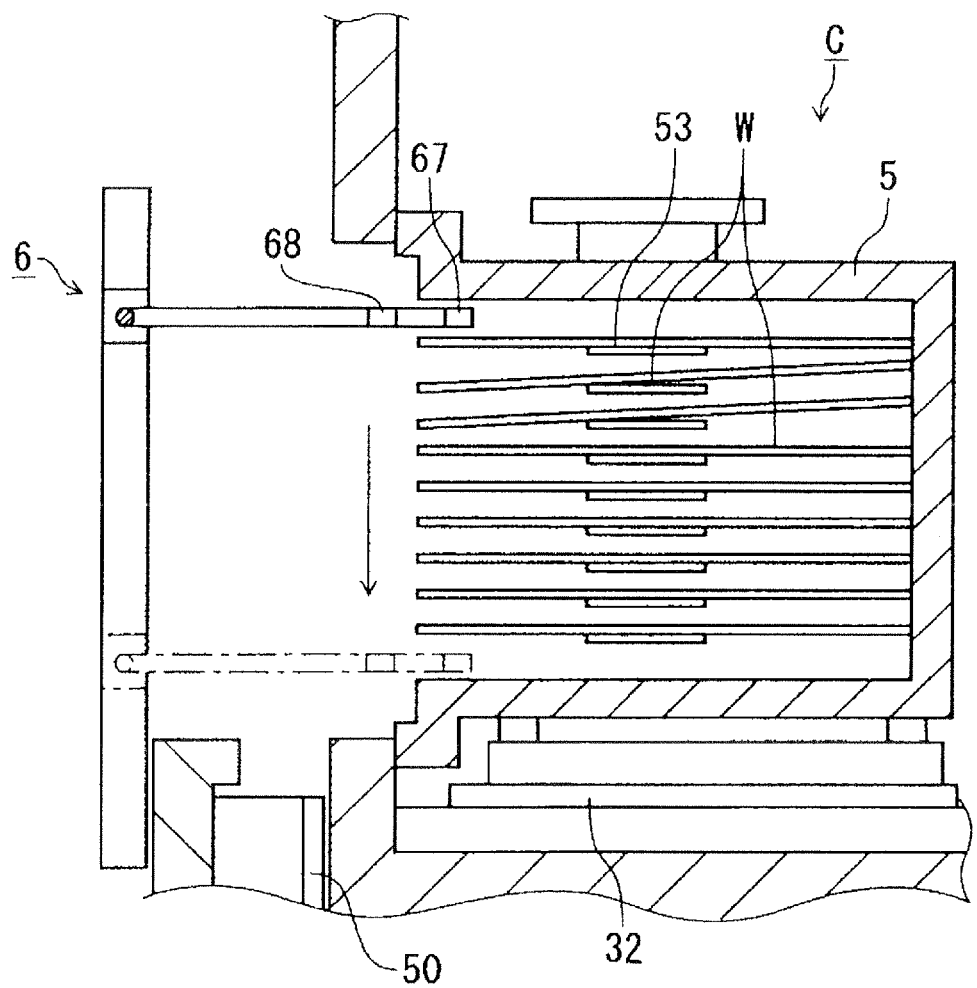
FIG. 18 is an explanatory drawing showing the wafer transfer between the carrier block and the carrier.

An explanation of abnormality detection is made for the case where (instead of the abnormal carrier C shown in FIG. 9) a normal carrier C in which the height position of each slot 500 is normal as shown in FIG. 8 is transported to the coating and developing apparatus 1. FIG. 17 shows the situation where the normal carrier C is subjected to the carry-in mapping in the same manner as described above. After the carry-in mapping, wafers W are carried into the coating and developing apparatus 1, and then the wafers W are returned into the carrier C by the transfer mechanism 16. It is assumed that, when the wafers W are returning into the carrier C and are being transferred to the support members 53, due to any failure of the transfer mechanism 16, some of the wafers W bounce on the support members 53 so as to be stored in the slots 500 in an inclined manner as shown in FIG. 18. In the example of FIG. 18, the wafers W in the slots 502 and 503 are inclined so that their height positions are deviated from the corresponding allowable ranges, and the carry-out mapping is performed under this condition.

Although omitted in the previous explanation, the apparatus controller 2, following to the judgment on presence or absence of abnormality of the carrier C, performs a judgment on presence or absence of abnormality of the transfer mechanism 16. The judgment on presence or absence of abnormality of the transfer mechanism 16 is described. It is judged whether or not there is a slot 500 that stores a wafer W at a height position within the allowable range when the carry-in mapping is performed but stores the wafer W at a height position out of the allowable range when the carry-out mapping is performed. If it is judged that there is such a slot 500, the transfer mechanism 16 is judged to have an abnormality. Then, an alarm informing the fact is outputted.

Figure 19:
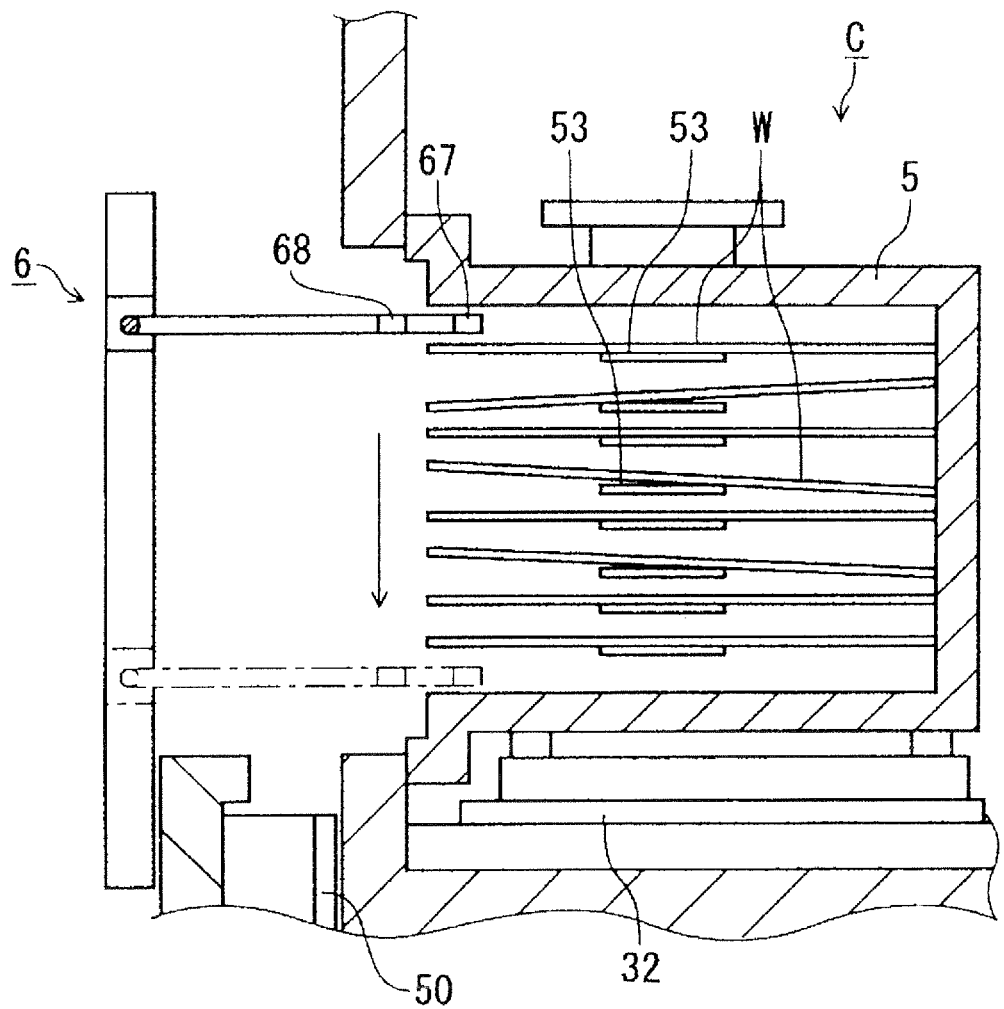
FIG. 19 is an explanatory drawing showing the wafer transfer between the carrier block and the carrier.

Even the slots of the carrier C have normal height positions as shown in FIG. 8, the carrier C may receive a shock, when the carrier C is transported by the carrier transport mechanism 12 to the coating and developing apparatus 1, when the carrier C is moved to the load position by moving the stage 32, and/or when the lid 50 of the carrier C is removed from the container main body 5. The shock may cause a wafer W to be obliquely supported by the support member 53 in such a manner that the lid 50 side portion of the wafer W is raised or lowered. The inclined state of the wafer W may be maintained because of the friction between the support member 53 and the back surface of the wafer W. This is the aforementioned abnormality at the loading. As shown in FIG. 19, the carry-in mapping may be performed under such a condition.

Figure 20:
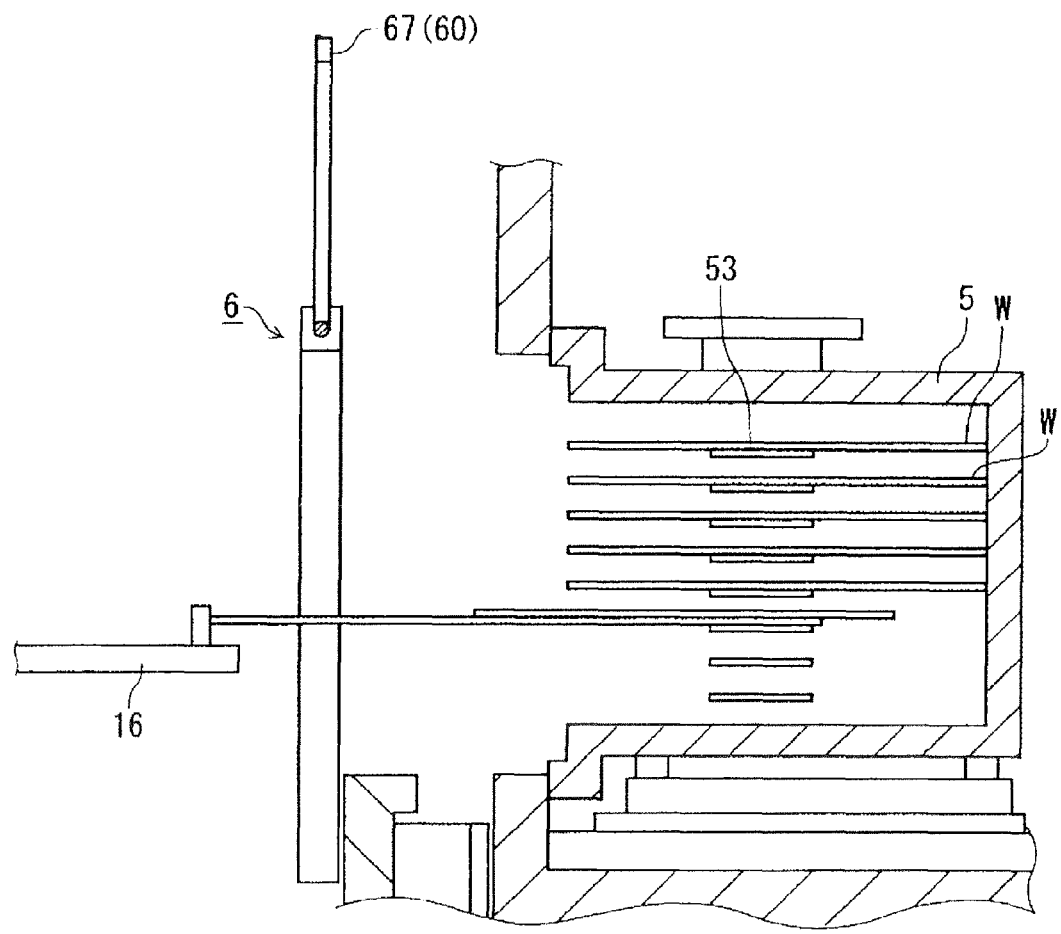
FIG. 20 is an explanatory drawing showing the wafer transfer between the carrier block and the carrier.
Figure 21:
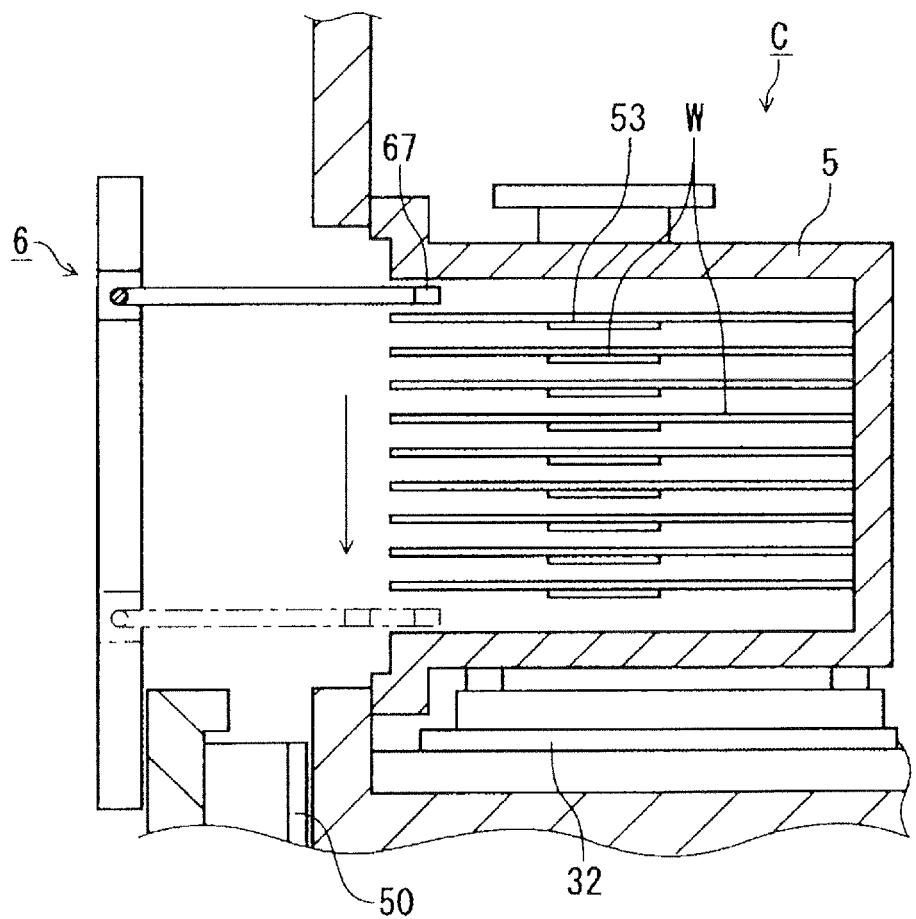
FIG. 21 is an explanatory drawing showing the wafer transfer between the carrier block and the carrier.

However, even in such a case, the wafer W is transported. When the wafer W is then returned to the carrier C after being processed, the wafer W is held horizontally as shown in FIG. 20 as long as the transfer mechanism 16 does not have the aforementioned abnormality. Then the carry-out mapping is performed as shown in FIG. 21. After the carry-out mapping, the apparatus controller 2 further performs judgment on presence or absence of abnormality of the carrier C and the judgment on presence or absence of abnormality of the transfer mechanism 16, and subsequently performs the judgment on presence or absence of the in-loading abnormality.

To be specific, the judgment on presence or absence of the in-loading abnormality judges whether or not the height position of a wafer W in a slot 500, which was deviated from the allowable range at the carry-in mapping, falls now within the allowable range at the carry-out mapping. If it is within the allowable range, it is judged that an in-loading abnormality occurred, in other words, it is judged that a wafer W was inclined when the carrier C was transported to the load position by the carrier transport mechanism 12 or the stage 32, or when the lid 50 is removed from the carrier C. Then, an alarm informing the judgment result is outputted.

In the coating and developing apparatus 1, the carry-in mapping and the carry-out mapping are performed, and the height position of the wafer W stored in each slot 500 is detected by these mappings. Based on each height position, presence or absence of abnormality of the height position of each slot 500 is judged. Thus, continuous use of an abnormal carrier C and the resultant wafer damage can be prevented. Therefore, throughput reduction of the semiconductor manufacturing apparatus can be prevented.

In addition, presence or absence of abnormality of the transfer mechanism 16 can also be judged by means of the carry-in mapping and the carry-out mapping. It is thus possible to quickly address the abnormality of the transfer mechanism 16 (e.g., inspection and repair of the transfer mechanism 16). Therefore, throughput reduction of the semiconductor manufacturing apparatus can be more reliably prevented. Furthermore, it is possible to judge whether or not an abnormality occurs when the carrier C is moved to the load position or when the lid 50 is opened. It is possible to rapidly detect an abnormality of the load port 3 and the carrier transport mechanism 12. Therefore, throughput reduction of the semiconductor manufacturing apparatus can be more reliably prevented.

<Second Embodiment>

Figure 22:
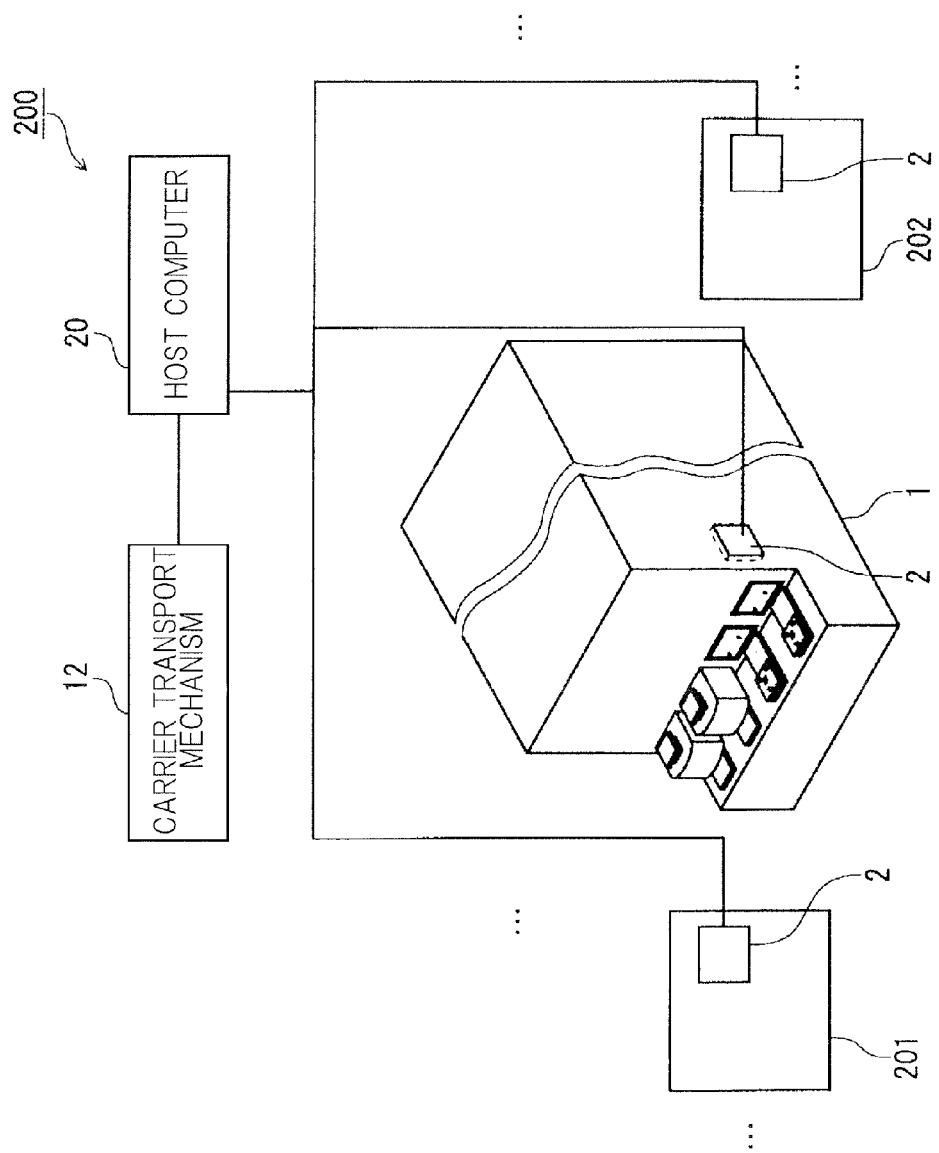
FIG. 22 is a block diagram of a substrate processing system including the coating and developing apparatus.

A substrate processing system 200 in a second embodiment is described with reference to FIG. 22. The substrate processing system 200 is constituted by interconnecting, through the host computer 20, the apparatus controllers 2 of a plurality of substrate processing apparatuses including the coating and developing apparatus 1. The substrate processing apparatuses includes: a cluster apparatus including an etching unit for performing dry etching and a film deposition unit for depositing a film by CVD or PVD; a vertical type heat treatment apparatus that collectively heats a number of wafers; an inspection apparatus that performs a predetermined inspection to wafers; and so on. These various processing apparatuses other than the coating and developing apparatus 1 have blocks corresponding to the carrier block E1. In these processing apparatuses, carriers C are transferred to and from the processing apparatus and wafers W are transferred to and from the carriers C, in a manner similar to that in the coating and developing apparatus 1. The reference numeral 201 depicts an apparatus to which a carrier C is transported and in which wafers W are processed there, just before the coating and developing apparatus 1. The reference numeral 202 depicts an apparatus to which the carrier C is transported and in which the wafers W are processed, just after the coating and developing apparatus 1.

In the substrate processing system 200, also in the processing apparatuses other than the coating and developing apparatus 1, carry-in mapping data and carry-out mapping data are obtained in the manner as mentioned above. Then, the carry-out mapping data obtained in one of the processing apparatuses, together with the ID number of the carrier C at which the carry-out mapping data are obtained, is transmitted through the host computer 20 to the apparatus controller 2 of another processing apparatus into which the carrier C is to be transported next to the one processing apparatus. That is, the carry-out mapping data obtained in the apparatus 201 is transmitted to the coating and developing apparatus 1, while the carry-out mapping data obtained in the coating and developing apparatus 1 are transmitted to the apparatus 202.

The apparatus controller 2 of one of the apparatuses, which has received the ID number of the carrier C and the carry-out mapping data from another apparatus, obtains carry-in mapping data of the carrier C having the same ID number in the one apparatus. Then, the apparatus controller of the one apparatus performs judgment on presence or absence of abnormality of the carrier C and judgment on presence or absence of the in-loading abnormality by using the carry-in mapping data and the carry-out mapping data, similarly to the first embodiment. That is, for example, the coating and developing apparatus 1 performs the above judgments by using the carry-out mapping data of the carrier C obtained in the apparatus 201, and the carry-in mapping data of the same carrier C obtained in the coating and developing apparatus 1. Due to such a configuration, the same advantages as those of the first embodiment can be achieved.

In the second embodiment, when the carry-in mapping is performed in the coating and developing apparatus 1, i.e., before wafers W are transported to the processing block E2 by the transfer mechanism 16, the apparatus controller 2 can recognize that a wafer W is inclined due to abnormality of the carrier C as shown in FIG. 9, or due to the in-loading abnormality (there is no abnormality of the carrier C) as shown in FIG. 19. If it is judged that the wafer inclination is not due to the abnormality of the carrier C but due to the in-loading abnormality, the wafers W may be reset (retry placing the wafer).

For the purpose of the resetting, the reflection sensor 68 is configured to also have a function of a distance sensor capable of detecting the distance between the reflection sensor 68 and a wafer W, based on reflected light from the wafer W. In addition, the apparatus controller 2 is configured to be capable of calculating the position of the center (center of gravity) of each wafer W based on the outputs of the reflection sensor 68 and the light receiving device 67. An example of the resetting of the wafer W is described below. With reference to the height position of each wafer W obtained by the carry-in mapping in the coating and developing apparatus 1, the tip end of the transfer mechanism 16 is advanced into a space below the inclined wafer W so as not to interfere with the wafers W stored in the carrier C.

When the tip end of the transfer mechanism 16 has reached a position which is slightly deeper from the center of the wafer W in the interior of the container main body 5, the advancing of the transfer mechanism 16 is stopped, and the transfer mechanism 16 is moved upward. Thus, the wafer W is moved apart from the support member 53 and is supported by the transfer mechanism 16 to take a horizontal posture. Thereafter, the transfer mechanism 16 is moved downward, so that the wafer W is horizontally held by the support member 53. If the central position of the wafer W whose inclination has been corrected is displaced from its prescribed position toward the opening 54, in other words, if the wafer W projects from the opening 54, the transfer mechanism 16 supports the wafer W to move the wafer W such that its central position is shifted deeper in the container main body 5, and then transfers the wafer W to the support member 53. After the inclination and projection of each wafer W have been corrected, the wafers W are sequentially carried out from the carrier C by the transfer mechanism 16. The above transport manner prevents the wafers W from being scratched by the transfer mechanisms 16.

The reflection sensor 68 detects the inclination of a wafer W with respect to the front and back direction, and the distance between the reflection sensor 68 and the wafer W. The sensor pair 60 detects the inclination of the wafer W with respect to the right and left direction. The central position of the wafer W is calculated based on the above detection results. Due to the operations that the central position of the wafer W is calculated and the transfer mechanism 16 is located slightly deeper in the carrier C from the central position, the horizontal posture on the transfer mechanism 16 can be achieved while suppressing the amount of insertion of the transfer mechanism 16 deep into the carrier C thereby preventing the wafer damage. In the resetting (re-placing) of the wafer W, the wafer W may be placed again, without calculating the central position, by moving the transfer mechanism 16 to a predetermined position in the container main body 5 and then by moving the transfer mechanism 16 upward. However in this case, in order to prevent the wafer W from being damaged, an amount of the forward movement the transfer mechanism 16 into the container main body 5 for the above resetting is set smaller than that for carrying out the wafer W form the container main body 5.

Figure 23:
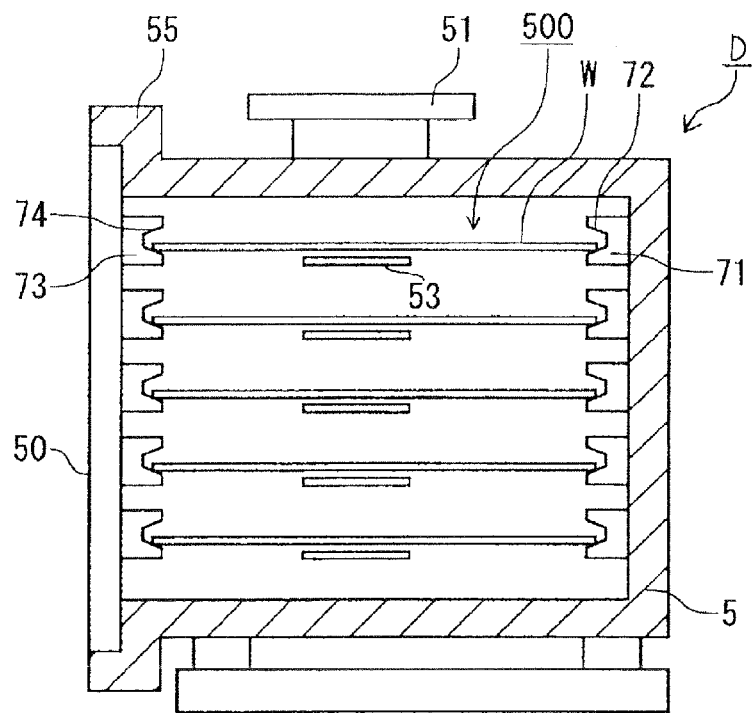
FIG. 23 is a vertically-sectioned side view of another carrier.

The structure of the carrier C used for practicing the present invention is not limited to the aforementioned structure, but may have a structure as shown in FIG. 23. A carrier D shown in FIG. 23 differs from the carrier C in that the carrier D has holding members 71 on the rear side of the container main body 5. Each holding member 71 is provided in respective ones of the slots 500, and is formed of a block having a cutout recessed toward the rear side. In addition, holding members 73 are provided on a rear side (the side facing the container main body 5) of the lid 50. Each holding member 73 is formed of a block having a cutout 74 recessed toward the front side of the lid 50. The peripheral portion of each wafer W is held by inclined faces defining these cutouts 72 and 74.

Figure 24:
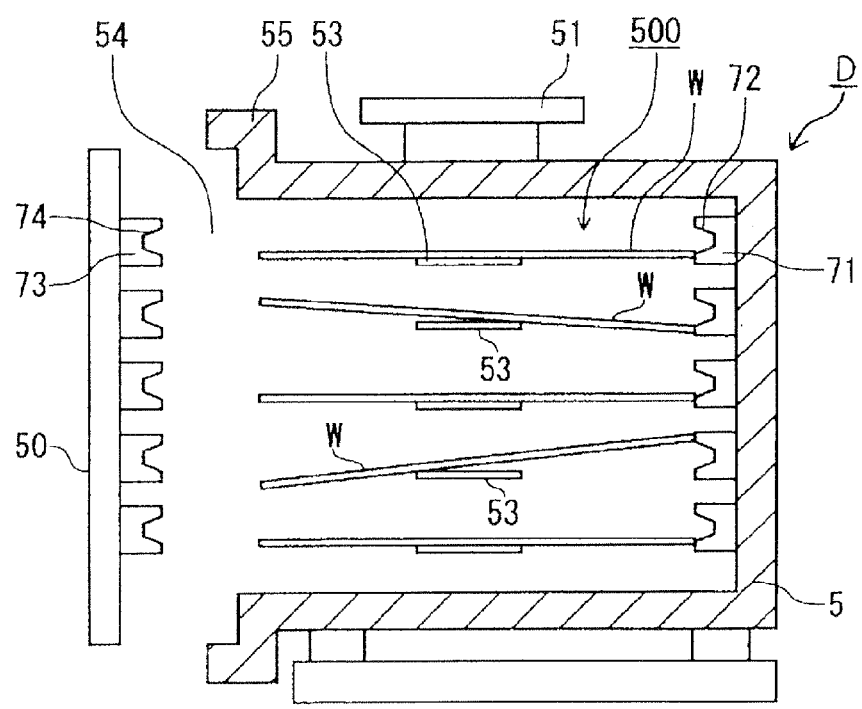
FIG. 24 is a vertically-sectioned side view of the carrier.

Similarly to the carrier C, there is a possibility also in the carrier D that, due to an impact exerted on the carrier D during transport of the carrier D or removal of the lid 50, the wafer W in the container main body 5 slips along the inclined face of the holding member 71 so as to be inclined such that the lid 50 side of the wafer W is raised, as shown in FIG. 24. The wafer W in the container main body 5 may be caught by the holding member 73 when the lid is removed, so that wafer W may be shifted with the movement of the lid 50 so as to be inclined such that the lid 50 side of the wafer W is lowered, as shown in FIG. 24. Therefore, also in the case where the carrier D is used, the use of the detection methods in the foregoing embodiments is advantageous.

In the foregoing embodiments, the height position of the wafer W is optically detected, but not limited thereto. In place of the sensor pair 60 and the reflection sensor 68, ultrasonic sensors may be provided on the elevation mechanism 61. In this case, the height position of the wafer W is detected by irradiating ultrasonic waves toward the wafer W while the ultrasonic sensors are moved upward or downward, and by detecting the ultrasonic waves collided with the wafer W to be reflected therefrom. Alternatively, the height position of the wafer W may be detected only by the reflection sensor 68 or the sensor pair 60.

If the mapping data can be transmitted between two or more apparatuses in the substrate processing system 200, the following operation of the system is possible. That is, the carrier C containing wafers W is firstly subjected to the carry-in mapping in one of the processing apparatuses. Then, after the wafers W are removed from the carrier C to the one processing apparatus, the carrier C is transported to another processing apparatus. The carry-in mapping data of the one processing apparatus are transmitted to the apparatus controller 2 of the another processing apparatus. Then, wafers W having been processed in the another apparatus are transported to the carrier C. At this time, based on the carry-in mapping data, the apparatus controller 2 can set the height positions according to which the transfer mechanism 16 of the another apparatus accesses the slots of the carrier C. Thus, the wafers W can be precisely stored into the carrier C.

The invention claimed is:

1. A substrate processing apparatus that removes substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, said substrate processing apparatus comprising:
   a load port into which the transport container is carried;
   a detecting unit that detects spatial positions of the substrates contained in the transport container, which has been carried into the load port and the lid of which has been removed;

a processing unit that processes the substrates removed from the transport container having been carried into the load port; and a control unit that performs a first step that detects spatial positions of the substrates contained in the transport container, which are in the transport container having been carried into the load port, before the substrates are removed from the transport container to be delivered to the processing unit; a second step that detects spatial positions of the substrates contained in the transport container, which have been processed in the processing unit and returned to the original transport container, before closing the lid; and a third step that judges whether or not the transport container has an abnormality based on results of the first and second steps.

2. The substrate processing apparatus according to claim 1, wherein the detecting unit includes a light sensor having a horizontal light axis that moves vertically relative to the transport container so as to obtain data on presence or absence of transmitted light correlated with height positions in the opening of the transport container.

3. The substrate processing apparatus according to claim 1, wherein the control unit judges that the transport container has an abnormality, if an abnormality of the spatial positions of the substrates is detected in the first step and if the same abnormality as that in the first step is detected in the second step.

4. The substrate processing apparatus according to claim 1, wherein the control unit judges that a transport system in the substrate processing apparatus has an abnormality, if an abnormality of the spatial positions of the substrates is detected in the second step and if an abnormality of the spatial positions of the substrates is not detected in the first step.

5. The substrate processing apparatus according to claim 1, wherein the control unit judges that an abnormality has occurred during transporting of the transport container or during removal of the lid, if an abnormality of the spatial positions of the substrates is detected in the first step and if an abnormality of the spatial positions of the substrates is not detected in the second step.

6. The substrate processing apparatus according to claim 1, wherein the control unit reports a judgment result to a host computer when the control unit judges that the transport container has an abnormality.

7. A method of operating a substrate processing apparatus that removes substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, said method comprising:

a step that carries the transporting container into the load port and removes the lid;

a first detecting step that thereafter detects spatial positions of the substrates contained in the transport container, before the substrates are delivered to a processing unit;

a step that thereafter removes the substrates from the transport container, processes the substrates in the processing unit, and contains the substrates into the transport container;

a second detecting step that thereafter detects spatial positions of the substrates contained in the transport container, before the lid is closed; and a judging step that judges whether or not the transporting container has an abnormality based on results of the first and second detecting steps.

8. The method of operating the substrate processing apparatus according to claim 7, wherein the first and second detecting steps each include a step that obtains data on presence or absence of transmitted light correlated with height positions in the opening of the transport container, by using a light sensor having a horizontal light axis that moves vertically relative to the transport container.

9. The method of operating the substrate processing apparatus according to claim 7, wherein the judging step includes a step of judging that the transporting container has an abnormality, if an abnormality of the spatial positions of the substrates is detected in the first detecting step and if the same abnormality as that in the first detecting step is detected in the second detecting step.

10. The method of operating the substrate processing apparatus according to claim 7, wherein the judging step includes a step of judging that a transport system in the substrate processing apparatus has an abnormality, if an abnormality of the spatial positions of the substrates is detected in the second detecting step and if an abnormality of the spatial positions of the substrates is not detected in the first detecting step.

11. The method of operating the substrate processing apparatus according to claim 7, wherein the judging step judges that an abnormality has occurred during transporting of the transport container or during removal of the lid, if an abnormality is detected in the first detecting step and if an abnormality is not detected in the second detecting step.

12. A non-transitory storage medium storing a program that is used for executing a method of operating a substrate processing apparatus that removes substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, and wherein the program is configured for execution of the operating method according to claim 7.

13. A method of operating a plurality of substrate processing apparatuses that each remove substrates from a transport container and processes the substrates, wherein the transport container has a container main body whose substrate removal opening formed in a front face of the container main body is air-tightly closed by a lid, and the transport container is configured to allow a plurality of the substrates to be transported while the substrates being contained in the transport container in a form like shelves, said method comprising:

a step that returns substrates having been processed in one of the substrate processing apparatuses to the transport container placed on a load port;

a carry-out inspecting step that thereafter detects spatial positions of the substrates contained in the transport container, before the lid is closed;

a step that thereafter closes the transport container, and carries the transport container into a load port of another one of the substrate processing apparatuses;

a step that thereafter removes the lid from the transport container;

a carry-in inspecting step that thereafter detects spatial positions of the substrates contained in the transport container, before the substrates are delivered to a processing unit; and a judging step that judges whether or not the transporting container has an abnormality based on results of the carry-out inspecting step and the carry-in inspecting step.

14. The method of operating the substrate processing apparatuses according to claim 13, wherein the carry-out inspecting step and the carry-in inspecting step each include a step of obtaining data on presence or absence of transmitted light correlated with height positions in the opening of the transport container, by using a light sensor having a horizontal light axis that moves vertically relative to the transport container.

15. The method of operating the substrate processing apparatuses according to claim 13, wherein the judging step includes a step of judging that the transporting container has an abnormality if the same abnormality is detected in the the carry-out inspecting step and the carry-in inspecting step.

16. The method of operating the substrate processing apparatuses according to claim 13, wherein the judging step judges that an abnormality has occurred during transporting of the transport container or during removal of the lid, if an abnormality of the spatial positions of the substrates is detected in the carry-in inspecting step and if an abnormality of the spatial positions of the substrates is not detected in the carry-out inspecting step.

\* \* \* \* \*